United States Patent
Kapec et al.

(10) Patent No.: US 8,950,629 B2
(45) Date of Patent: Feb. 10, 2015

(54) DEVICE FOR DELIVERING ADHESIVE

(75) Inventors: Jeffrey S. Kapec, Westport, CT (US);
Kazuna Tanaka, Cos Cob, CT (US);
Yukiko Naoi, New York, NY (US);
Kenneth Allen Focht, Needham, MA (US); Gerhard Liepold, Watchung, NJ (US)

(73) Assignee: Cohera Medical, Inc., Pittsburgh, PA (US)

( * ) Notice: Subject to any disclaimer, the term of this patent is extended or adjusted under 35 U.S.C. 154(b) by 233 days.

(21) Appl. No.: 12/783,378

(22) Filed: May 19, 2010

(65) Prior Publication Data

US 2011/0062189 A1    Mar. 17, 2011

Related U.S. Application Data

(60) Provisional application No. 61/179,632, filed on May 19, 2009.

(51) Int. Cl.
*B05C 17/01* (2006.01)
*A61B 17/00* (2006.01)
*A61M 35/00* (2006.01)

(52) U.S. Cl.
CPC ........ *A61B 17/00491* (2013.01); *A61M 35/003* (2013.01)
USPC .............. 222/82; 222/327; 222/330; 222/391

(58) Field of Classification Search
CPC ................. A61M 35/003; A61B 17/00491
USPC .................................. 222/82, 327, 330, 391
See application file for complete search history.

(56) References Cited

U.S. PATENT DOCUMENTS

| | | | | |
|---|---|---|---|---|
| 2,725,877 A | * | 12/1955 | Reiter et al. | 604/135 |
| 4,099,482 A | * | 7/1978 | Smrt | 118/712 |
| 5,441,583 A | * | 8/1995 | Eaton et al. | 156/71 |
| 5,503,302 A | * | 4/1996 | DeJonge | 222/82 |
| 5,735,437 A | * | 4/1998 | Broyles et al. | 222/137 |
| 5,875,920 A | * | 3/1999 | Parent | 222/1 |
| 5,882,133 A | * | 3/1999 | Chao et al. | 401/266 |
| 6,024,250 A | * | 2/2000 | Hickey | 222/63 |
| 6,981,611 B2 | * | 1/2006 | Carruth et al. | 222/1 |
| 7,748,920 B2 | * | 7/2010 | Murray | 401/11 |

(Continued)

FOREIGN PATENT DOCUMENTS

| | | |
|---|---|---|
| CN | 1826181 | 8/2006 |
| GB | 2367864 | 4/2002 |

(Continued)

OTHER PUBLICATIONS

International Search Report and Written Opinion in International Application No. PCT/US2010/035452, dated Feb. 22, 2011, 22 pages.

(Continued)

*Primary Examiner* — Daniel R Shearer
(74) *Attorney, Agent, or Firm* — Fish & Richardson P.C.

(57) ABSTRACT

This document relates to delivery devices for dispensing fluid materials, including high viscosity fluids such as high viscosity surgical adhesives. For example, methods and materials for an integrated system of containing and permitting point of use delivery of a high viscosity adhesive fluid onto a planar surface of tissue during a surgical procedure are provided.

18 Claims, 23 Drawing Sheets

(56) References Cited

U.S. PATENT DOCUMENTS

| | | | |
|---|---|---|---|
| 2004/0230157 A1 | 11/2004 | Perry et al. | |
| 2005/0173019 A1 | 8/2005 | Navarro | |
| 2006/0111738 A1 | 5/2006 | Wenchell | |
| 2006/0118580 A1* | 6/2006 | Spencer | 222/327 |
| 2008/0103564 A1 | 5/2008 | Burkinshaw et al. | |
| 2009/0272759 A1* | 11/2009 | Bambrick et al. | 222/1 |
| 2010/0237104 A1* | 9/2010 | Schneider et al. | 222/330 |

FOREIGN PATENT DOCUMENTS

| | | |
|---|---|---|
| GB | 2410909 | 8/2005 |
| GB | 2443271 | 4/2008 |
| JP | 2001-518387 | 10/2001 |
| JP | 2004-517663 | 6/2014 |
| SU | 1516117 | 10/1989 |
| WO | WO 2006/024094 | 3/2006 |
| WO | WO2007/122006 | 11/2007 |

OTHER PUBLICATIONS

International Preliminary Report on Patentability in International Application No. PCT/US2010/035452, dated Nov. 22, 2011, 8 pages.

Abraham et al. "Trimolecular complexes of lambda light chain dimers in serum of a patient with multiple myeloma," *Clinical Chemistry*, 2002, 48(10):1805-1811.

Kosaka et al. "Tetramer Bence Jones protein in the immunoproliferative disease. Angioimmunoblastic lymphadenopathy, primary amyloidosis, and multiple myeloma," *American Journal of Clinical Pathology*, 1989, 91(6): 639-646.

Myatt et al. "Pathogenic potential of human monoclonal immunoglobulin light chains: relationship of in vitro aggregation to in vivo organ deposition," *Proceedings of the National Academy of Sciences. USA.* 1994, 91(8):3034-3038.

Palladini et al. "Identification of amyloidogenic light chains requires the combination of serum-free light chain assay with immunofixation of serum and urine," *Clinical Chemistry.* 2009, 55(3):499-504.

* cited by examiner

DEVICE FOR DELIVERING ADHESIVE

CROSS-REFERENCE TO RELATED APPLICATIONS

This application claims the benefit of U.S. Provisional Application Ser. No. 61/179,632, filed May 19, 2009. The disclosure of the prior application is considered part of (and is incorporated by reference in) the disclosure of this application.

BACKGROUND

1. Technical Field

This document relates to delivery devices for dispensing fluid materials, including high viscosity fluids such as high viscosity surgical adhesives.

2. Background Information

Biological and synthetic tissue adhesives have been developed as alternatives to sutures and staples for adhering biological tissue. Examples of biological tissue adhesives include fibrin sealants, which can be used externally or internally for wound closure and sealing. Such fibrin sealants are typically formed using two reactive components that are combined in a chemical process, for example, immediately before dispensation from a double-barrel syringe.

SUMMARY

This document provides methods and materials related to dispensing a high viscosity fluid. For example, this document provides an integrated system that permits point of use delivery of a high viscosity adhesive fluid onto planar surfaces of tissue during a surgical procedure. In some embodiments, a delivery device provided herein can be used to deliver a defined volume of adhesive onto a targeted anatomical site at a defined spacing. The delivery devices provided herein can overcome resistance of high viscosity fluids with an internal mechanism that can amplify the forces deployed by a user's finger or hand. For example, the delivery technique provided herein can be administered by one hand without the need of additional equipment, pumps, pressure assist, or electromechanical devices. As described herein, a delivery device provided herein can provide a surgeon or other clinician with a tool for dispensing multiple drops of adhesive in a uniform, defined volume and in defined spacing intervals.

Some of the embodiments described herein may provide one or more of the following advantages. A delivery device provided herein can be used to deliver a viscous fluid, such as a high viscosity surgical adhesive, to a targeted tissue site in a controlled and reliable manner. In such circumstances, the delivery device may be operated by a surgeon or other medical practitioner to dispense drops of the surgical adhesive selectively (e.g., when the surgeon or other medical practitioner activates an actuator on the delivery device).

The delivery devices provided herein can be used as single-use instruments suitable for use in a surgical environment. For example, a delivery device provided herein can be disposable and non-reusable such that the delivery device is discarded after a single use. Such a configuration can reduce likelihood of contamination and can reduce or eliminate the burden of cleaning and reassembling parts of a delivery instrument. In some circumstances, a delivery device provided herein can contain a predetermined volume of the viscous fluid so as to encourage the single-use operability.

In some cases, a delivery device provided herein can have an applicator portion including the handle that is reusable and not limited to a single use. For example, a non-disposable and reusable applicator portion of the delivery device can be used with disposable and non-reusable delivery tips and adhesive cartridges. Such a configuration can reduce or eliminate the need to replace the entire delivery device when the viscous fluid has been depleted or the application procedure is completed.

The delivery devices provided herein can be used to dispense an adhesive made of components that are premixed and stored in an adhesive cartridge housing of the delivery device. As such, the delivery device can promptly dispense the adhesive fluid without the requirement of mixing two reactive chemical components immediately before delivery. In some cases, a delivery device provided herein can provide a single-button operation that causes the release of the viscous fluid from its reservoir.

One or more delivery devices can be part of a packaged system that permits the delivery devices to be readily available to a user in a safe and reliable manner. For example, the system can include a set of the delivery devices (e.g., two, three, four, five, six, or more delivery devices) arranged in a surgical storage module that fits within a surgical instrument rack arranged in an operating room. Accordingly, the surgical storage module (having the new delivery devices contained therein) can be readily received from a supplier and then fit into the surgical instrument rack for immediate or subsequent use in a surgical environment. Such a configuration can reduce the burden of staff workers responsible for material handling and inventory restocking.

In general, one aspect of this document features a delivery device for applying two or more drops of a viscous fluid to a surface. The delivery device comprises, or consists essentially of, (a) an actuator portion comprising an actuator and a push rod, wherein the actuator portion is configured to advance the push rod when a user actuates the actuator, (b) a cartridge housing configured to receive a cartridge containing the viscous fluid, wherein the cartridge housing is attached to the actuator portion such that the push rod is capable of advancing into the cartridge when the cartridge is positioned within the cartridge housing, and (c) a tip releasably engaged to the cartridge housing, wherein the tip comprises two or more tubular members configured to allow the viscous fluid to move from the cartridge to the surface when the user actuates the actuator, wherein a single actuation of the actuator is capable of dispensing a single drop of the viscous fluid from each of the tubular members at the same time, wherein the volume of each of the dispensed drops is substantially similar. The viscous fluid can have a viscosity of 1000 cP. The surface can be a surface of a human body. The surface can comprise human tissue. The actuator portion can comprise a handle. The actuator can be a trigger or button. The push rod can comprise a plunger attached to the distal end of the push rod. The cartridge housing can be cylindrical. The push rod can be capable of advancing into the cartridge when a user actuates the actuator and can be capable of retreating when the user releases the actuator. The push rod can be capable of advancing into the cartridge when a user actuates the actuator and can be restricted from retreating when the user releases the actuator. The tip can comprise three tubular members configured to allow the viscous fluid to move from the cartridge to the surface when the user actuates the actuator. The distal tips of the tubular members can be configured in a linear line and can be sequentially spaced apart from each other at a substantially similar distance. The tip can comprise a spacing gauge configured to allow the user to align a second set of dispensed drops a predefined distance from a first set of dispensed drops. A distal tip of the spacing gauge can be positioned, from the linear line, at a distance similar to the substantially similar distance. The tip can comprise a support for each of the tubular members. The supports can be configured to form a channel for the tubular members. The tubular members can have an inner diameter between 0.011 inches and 0.025 inches. The tip can comprise a spacing gauge configured to allow the user to align a second set of dispensed drops a predefined distance from a first set of dispensed drops. The cartridge can comprise a distal end, a proximal end, and a plunger located within the cartridge near to the proximal end, the proximal end can comprise a seal, and the push rod can be configured to engage the plunger. A distal end of the push rod can comprise a seal piercing element. The seal piercing element can comprise at least six extensions. The seal piercing element can be configured to pierce the seal of the proximal end of the cartridge. The cartridge can comprise a distal end and a proximal end, the distal end can comprise a seal, and a distal portion of the delivery device can comprise a piercing element configured to pierce the seal of the distal end of the cartridge as the cartridge is advanced from one location within the delivery device toward the distal end of the delivery device. The delivery device can comprise an actuator ring configured to advanced the cartridge from one location within the delivery device toward the distal end of the delivery device as the actuator ring is rotated.

In another aspect, this document features a delivery device for applying two or more drops of a viscous fluid to a surface. The delivery device comprises, or consists essentially of, (a) a push rod, (b) an actuator, wherein the actuator is configured to advance the push rod when a user actuates the actuator, (c) a cartridge housing portion configured to house a cartridge containing the viscous fluid, wherein the push rod is capable of advancing into the cartridge when the cartridge is positioned within the cartridge housing, and (d) a tip located at a distal end of the delivery device, wherein the tip comprises two or more tubular members configured to allow the viscous fluid to move from the cartridge to the surface when the user actuates the actuator, wherein a single actuation of the actuator is capable of dispensing a single drop of the viscous fluid from each of the tubular members at the same time, wherein the volume of each of the dispensed drops is substantially similar. The viscous fluid can have a viscosity of 1000 cP. The surface can be a surface of a human body. The surface can comprise human tissue. The delivery device can comprise a handle. The actuator can be a trigger or button. The push rod can comprise a plunger attached to the distal end of the push rod. The cartridge housing can be cylindrical. The push rod can be capable of advancing into the cartridge when a user actuates the actuator and can be capable of retreating when the user releases the actuator. The push rod can be capable of advancing into the cartridge when a user actuates the actuator and can be restricted from retreating when the user releases the actuator. The tip can comprise three tubular members configured to allow the viscous fluid to move from the cartridge to the surface when the user actuates the actuator. The distal tips of the tubular members can be configured in a linear line and are sequentially spaced apart from each other at a substantially similar distance. The tip can comprise a spacing gauge configured to allow the user to align a second set of dispensed drops a predefined distance from a first set of dispensed drops. A distal tip of the spacing gauge can be positioned, from the linear line, at a distance similar to the substantially similar distance. The tip can comprise a support for each of the tubular members. The supports can be configured to form a channel for the tubular members. The tubular members can have an inner diameter between 0.011 inches and 0.025 inches. The tip can comprise a spacing gauge configured to allow the user to align a second set of dispensed drops a predefined distance from a first set of dispensed drops. The cartridge can comprise a distal end, a proximal end, and a plunger located within the cartridge near to the proximal end, the proximal end can comprise a seal, and the push rod can be configured to engage the plunger. A distal end of the push rod can comprise a seal piercing element. The seal piercing element can comprise at least six extensions. The seal piercing element can be configured to pierce the seal of the proximal end of the cartridge. The cartridge can comprise a distal end and a proximal end, the distal end can comprise a seal, and a distal portion of the delivery device can comprise a piercing element configured to pierce the seal of the distal end of the cartridge as the cartridge is advanced from one location within the delivery device toward the distal end of the delivery device. The delivery device can comprise an actuator ring configured to advanced the cartridge from one location within the delivery device toward the distal end of the delivery device as the actuator ring is rotated.

In another aspect, this document features a method for applying two or more drops of a viscous fluid to a surface. The method comprises, or consists essentially of, actuating an actuator of a delivery device one or more times. The delivery device comprises, or consists essentially of, (a) a push rod, (b) the actuator, wherein the actuator is configured to advance the push rod when a user actuates the actuator, (c) a cartridge housing portion configured to house a cartridge containing the viscous fluid, wherein the push rod is capable of advancing into the cartridge when the cartridge is positioned within the cartridge housing, and (d) a tip located at a distal end of the delivery device, wherein the tip comprises two or more tubular members configured to allow the viscous fluid to move from the cartridge to the surface when the user actuates the actuator, and wherein a single actuation of the actuator dispenses a single drop of the viscous fluid from each of the tubular members at the same time, wherein the volume of each of the dispensed drops is substantially similar.

In another aspect, this document features a system for filling a cartridge with a viscous fluid. The system comprises, or consists essentially of, (a) a vessel comprising the viscous fluid, wherein the viscous fluid in the vessel is under pressure greater than 20 psi and has a temperature no more than 5° C., (b) a cartridge configured to receive the viscous fluid, and (c) a flow path for delivering the viscous fluid from the vessel to the cartridge, wherein the diameter of the flow path is the same from the vessel to the cartridge. The pressure can be about 40 psi. The vessel can hold a volume of between 0.5 L and 1.5 L. The viscous fluid can have a viscosity of 1000 cP. The flow path can comprise a silicone tube. The system can comprise a pinch valve attached to the flow path to stop movement of the viscous fluid from the vessel to the cartridge.

In another aspect, this document features a method for filling a cartridge with a viscous fluid. The method comprises, or consists essentially of, allowing the viscous fluid to flow along a flow path from a vessel comprising the viscous fluid to the cartridge, wherein the viscous fluid in the vessel is under pressure greater than 20 psi and has a temperature no more than 5° C., and wherein the diameter of the flow path is the same from the vessel to the cartridge.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document provides methods and materials related to dispensing a viscous fluid. As described herein, a delivery device provided herein can be used to deliver multiple drops of a viscous fluid simultaneously such that each drop contains a uniform, defined volume and is dispensed at a defined spacing.

Figure 1:
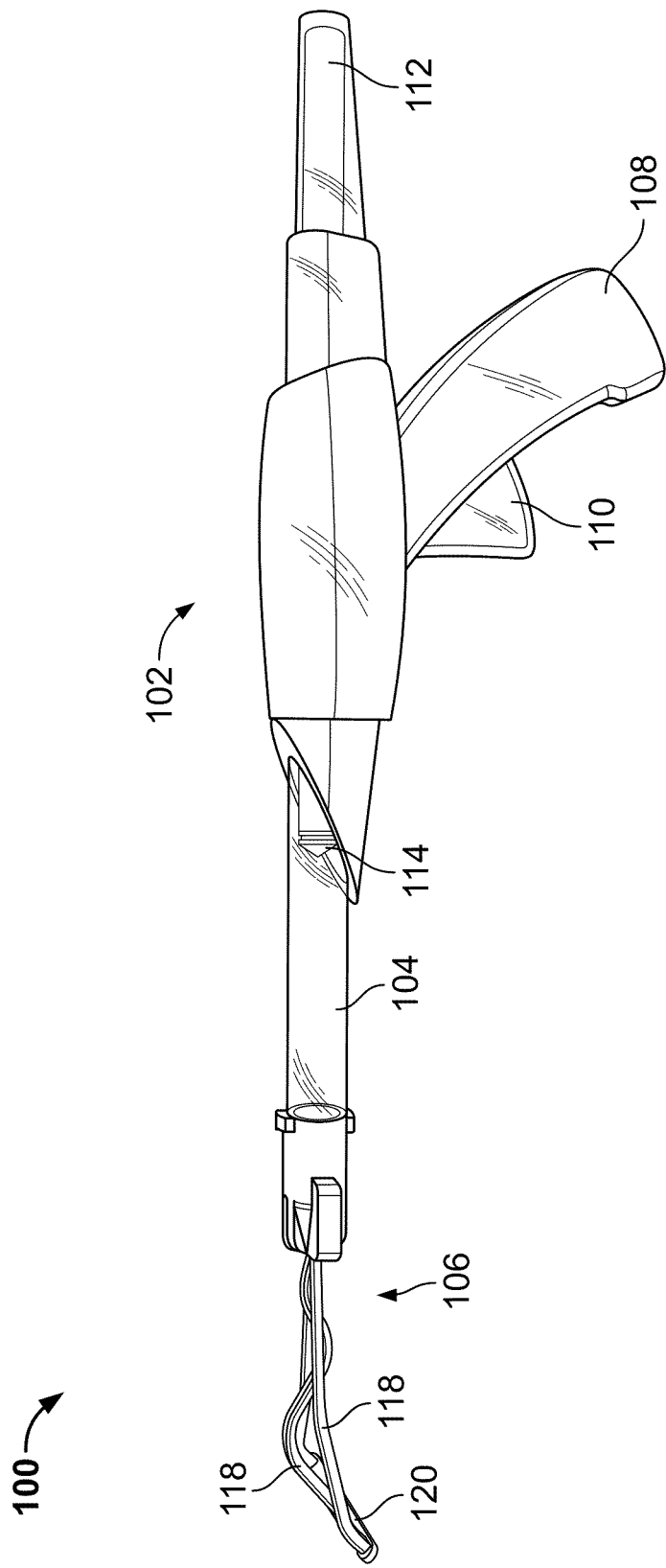
FIG. 1 is a side perspective view of an exemplary delivery device in accordance with some embodiments.

Referring to FIG. 1, delivery device 100 can have applicator portion 102. Applicator portion 102 can be configured to engage cartridge housing 104 such that a push rod located within applicator portion 102 can be advanced into an adhesive cartridge (not shown) that is positioned within cartridge housing 104. Cartridge housing 104 can be configured to engage delivery tip 106 such that a viscous fluid maintained in an adhesive cartridge of cartridge housing 104 can be advanced to delivery tip 106. Applicator portion 102 can have handle 108, which can be configured to fit comfortably in a user's hand. Handle 108 can include actuator 110. Actuator 110 can be pushed or depressed by a user such that actuator 110 moves relative to a handle mechanism. In some cases, actuator 110 can be configured as a trigger, button, or other mechanism that can be moved by a user applying force using one or more fingers. The user can apply force to actuator 110 in order to engage an internal handle mechanism. The internal handle mechanism can be designed to advance push rod 112. Push rod 112 can be configured to engage plunger 114 in a manner that pushes and/or pulls plunger 114 inside an adhesive cartridge located with cartridge housing 104. Cartridge housing 104 can be configured to house an adhesive cartridge (not shown) and to engage delivery tip 106 in a manner that allows a viscous fluid to move from an adhesive cartridge through channels or tubes of tip 106. Delivery tip 106 can have one or more supports 118 and brace 120. Brace 120 can have a generally cylindrical shape, a generally rectangular shape, or any other appropriate shape. Any appropriate material can be used to make actuator 110, handle 108, cartridge housing 104, delivery tip 106, supports 118, and brace 120. Such components can be made using, for example, plastic (e.g., polyethylene, high density polyethylene, polyvinyl chloride, polypropylene), metal (e.g., steel, titanium, aluminum), or glass (e.g., soda-lime glass, borosilicate glass, aluminosilicate glass).

Figure 2:
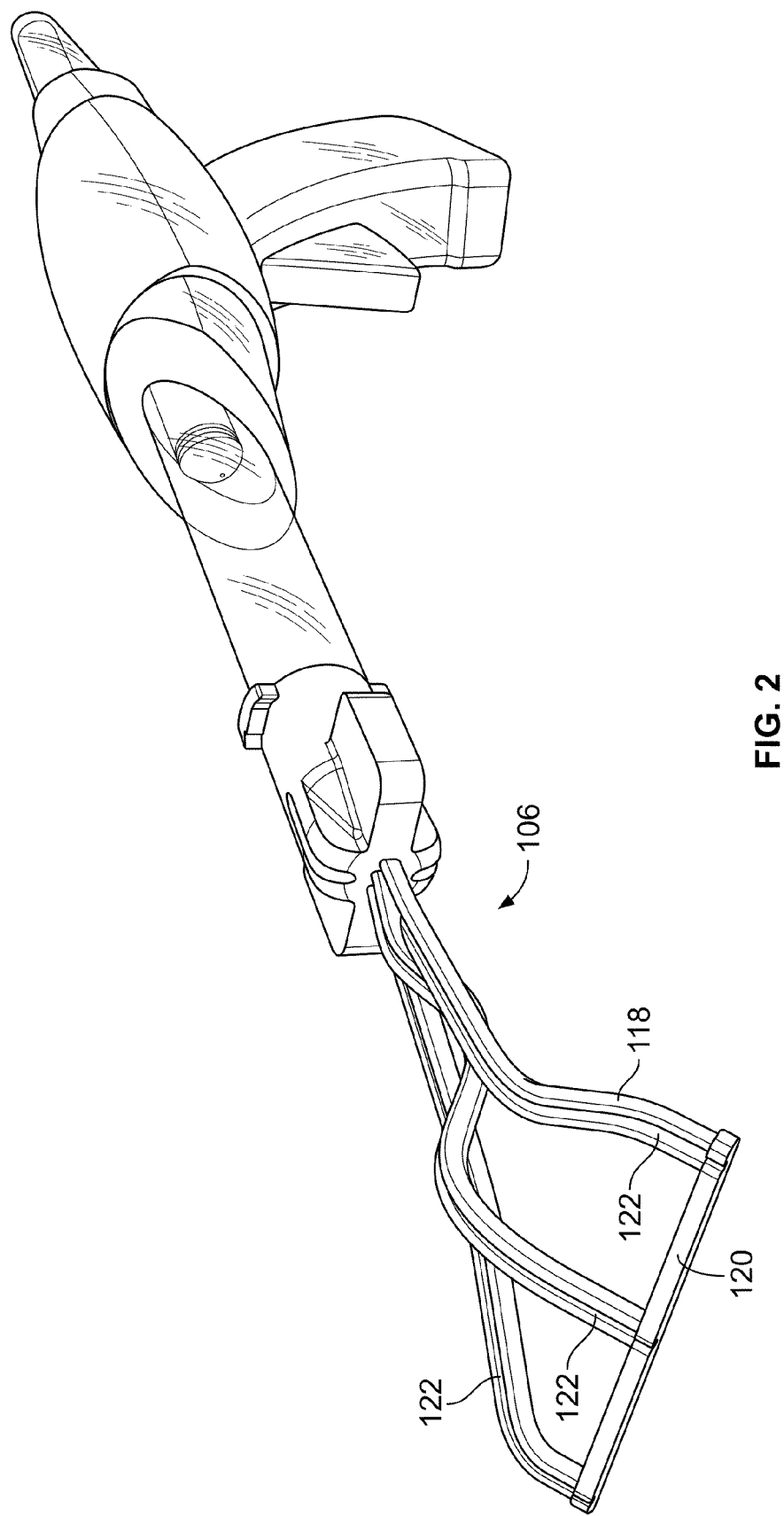
FIG. 2 is a partial front, side perspective view of the exemplary delivery device of FIG. 1.

Referring to FIGS. 1 and 2, delivery device 100 can include delivery tip 106 mounted to the distal end of cartridge housing 104. Delivery tip 106 can be configured to include any appropriate number of supports (e.g., 1, 2, 3, 4, 5, 6, 7, 8, 9 or more supports) configured to support a tubular member for delivering a viscous fluid from an adhesive cartridge to a target site (e.g., skin lesion or surgical site). Supports 118 can have a generally cylindrical shape, a generally rectangular shape, or any other appropriate shape. Support 118 can include channel 122, which is configured to support a tubular member. Channel 122 can be, for example, a closed or open channel. In some cases, channels 122 can be configured to permit delivery of a viscous fluid in a dimensionally controlled repeatable pattern without the use of a tubular member. In some embodiments, supports 118 are of equal length. In such circumstances, drops of a highly viscous fluid that originate at the proximal ends of supports 118 will reach the distal end and delivery drops at the same time and at predetermined spacing. As demonstrated in FIG. 2, one or more supports 118 can have an S-shape or other non-linear shape in order to create supports of equal length. In some embodiments, brace 120 can separate supports 118 by a defined space. For example, supports 118 can be spaced between about 0.5 and 25 cm apart (e.g., about 0.5, 0.75, 1, 1.5, 2, 2.5, 3, 3.5, 4, 4.5, or 5 cm apart). The spacing of supports 118 of delivery tip 106 can permit a user to deliver a precise volume of a viscous fluid onto a surface (e.g., a planar surface) at predetermined positions equal to the number of supports. In some embodiments, delivery tip 106 can have three supports spaced about 2 cm apart in order to deliver three drops of a viscous fluid spaced about 2 cm apart on a planar surface.

In some cases, delivery device 100 can be configured to have an adhesive cartridge in place of cartridge housing 104. In such cases, delivery tip 106 can be attached (e.g. permanently attached, welded, or releasable attached) to the distal end of an adhesive cartridge.

Figure 3:
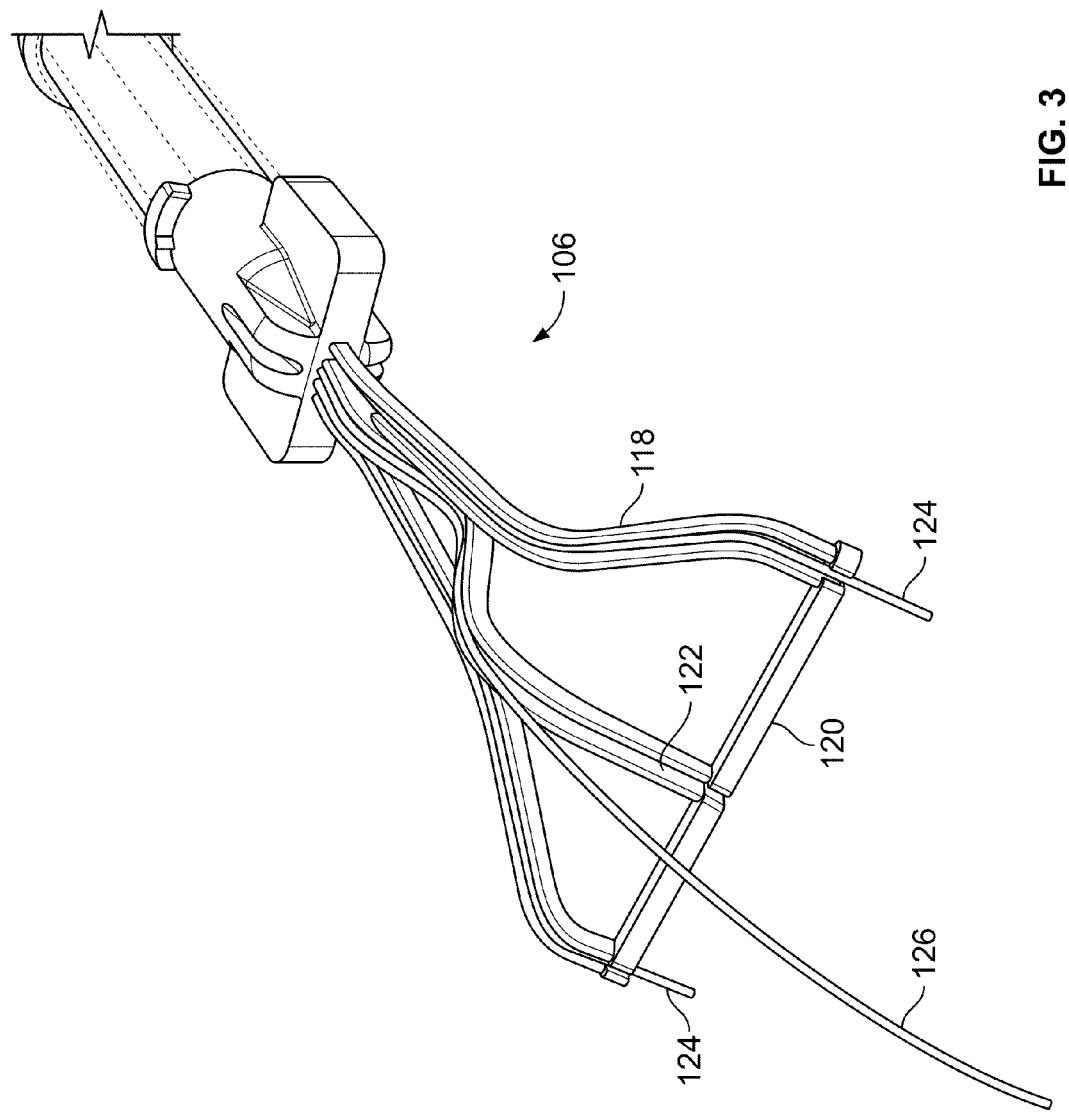
FIG. 3 is an enlarged perspective view of a portion of the exemplary delivery device of FIG. 1.

Referring to FIG. 3, channels 122 can have tubular member 124. In some embodiments, tubular member 124 can have the same length as channel 122. In some embodiments, tubular member 124 can extend beyond the distal end of channel 122 and beyond brace 120. Tubular members 124 in each support 118 can be of equal lengths. In such circumstances, drops of a highly viscous fluid that originate at the proximal ends of tubular members 124 will reach the distal end and delivery drops at the same time and at positions pre-determined by the spacing of supports 118. Tubular member 124 can be made from any appropriate material. For example, tubular member 124 can be a flexible polymer material (e.g., polyimide, polyethylene, polypropylene, PTFE, or PTFE/FEP composite constructions). In some cases, a tubular member can be made of MicroLumen® medical tubing (MicroLumen, Tampa, Fla.). Tubular member 124 can have any appropriate inner diameter. For example, the inner diameter can be between 0.005 and 0.1 inches (e.g., between 0.005 and 0.05 inches, between 0.01 and 0.05 inches, between 0.02 and 0.05 inches, between 0.005 and 0.04 inches, or between 0.01 and 0.04 inches). In some cases, the inner diameter can be 0.0129 inches, 0.0151 inches, or 0.0299 inches. For example, the inner diameter can be 0.0152 inches to deliver 0.038 µL drops of adhesive when the adhesive viscosity is between about 500-2000 cP (e.g., 250, 400, 500, 750, 1000, 1250, 1500, 1750, or 2000 cP). Tubular member 124 can have any appropriate outer diameter. For example, the outer diameter can be between 0.01 and 0.5 inches (e.g., 0.021 inches, 0.023 inches, 0.025 inches). In some embodiments, tubular member 124 can have an outer diameter that is smaller than the inner diameter of channel 122. Upon actuation of delivery device 100, tubular member 124 can advance drops of a viscous fluid to the distal portion of delivery tip 106.

Delivery tip 106 can include spacing gauge 126. In some embodiments, spacing gauge 126 can extend from the midline of delivery tip 106 and extend beyond brace 120 by a predetermined length between about 0.5 and about 25 cm (e.g., 0.5, 1, 1.5, 2, 2.5, 3, 4, 5, 6, 7, 8, 9, 10, 11, 12, 13, 14, 15, 18, 20, 22, 23, 25 cm). In some cases, the distance of the distal tip of spacing gauge 126 from brace 120 can be equal or similar to the distance between the distal tips of tubular members 124. Any appropriate material can be used to make spacing gauge 126. For example, spacing gauge 126 can be made using plastic, metal, glass, or composite materials. In some embodiments, delivery tip 106 can have three supports spaced about 2 cm apart and one spacing gauge 126 positioned about 2 cm in front of or behind brace 120 in the same plane. In such circumstances, delivery device 100 can deliver three drops of a viscous fluid spaced about 2 cm apart on a surface (e.g., a planar surface). Also, spacing gauge 126 can be used to position the device to deliver another row of drops at a predetermined distance (e.g., 0.5, 1, 1.5, 2, 2.5 cm) in front of or behind the first row. The number of drops delivered per actuation can depend on the number of supports and tubular members of delivery tip 106. For example, delivery tip 106 with four supports 118 can deliver a row of four drops.

Figure 4:
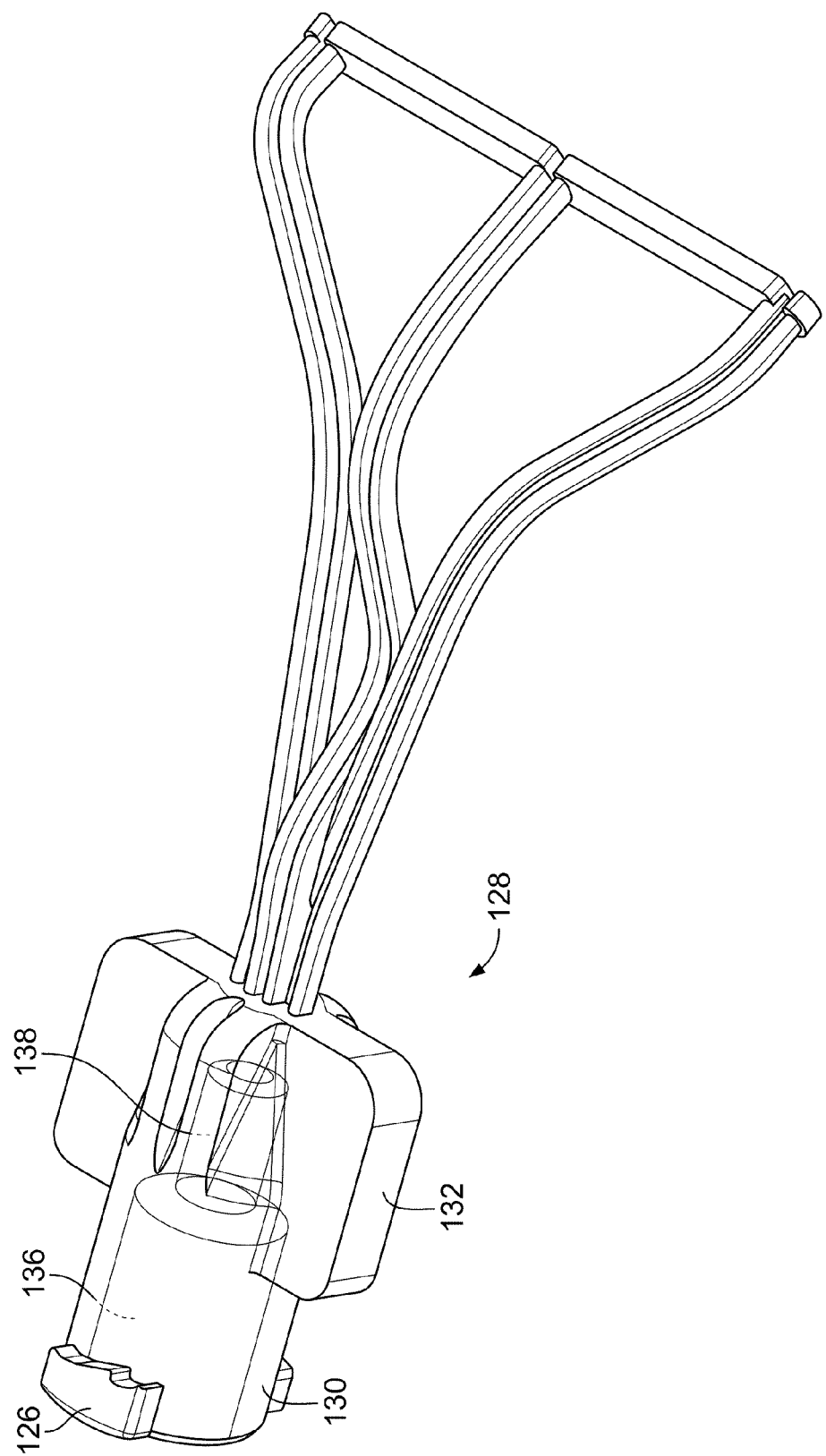
FIG. 4 is an enlarged perspective view of a portion of the exemplary delivery device of FIG. 1.

Referring to FIG. 4, cartridge housing 104 can be configured to engage delivery tip 106 by a positive engagement. The positive engagement can be, for example, a locking mechanism on the distal end of delivery tip 106. In some embodiments, locking mechanism 126 can be a Luer lock connector. Other appropriate locking mechanisms can include, for example, a custom designed cam locking system, a bayonet locking system, a screw thread with detent locking system, or permanent bonding and fixation of delivery tip 106. Delivery tip 106 can include hub 128 having connecting portion 130 and housing portion 132. Housing portion 132 of hub 128 can have any appropriate shape such as, for example, a generally rectangular box shape. The generally rectangular box shape can have rounded edges. Connecting portion 130 can be configured to engage cartridge housing 104 such that first channel 136 is formed. First channel 136 can be generally cylindrical or generally conical transitioning to a cylindrical shape. First channel 136 can be configured to narrow into intermediate channel 138 having a smaller diameter and generally cylindrical in shape. Intermediate channel 138 can be configured to engage the proximal ends of tubular members 124 such that a viscous fluid can be advanced from an adhesive cartridge (not shown) to the distal end of delivery tip 106.

Figure 5:
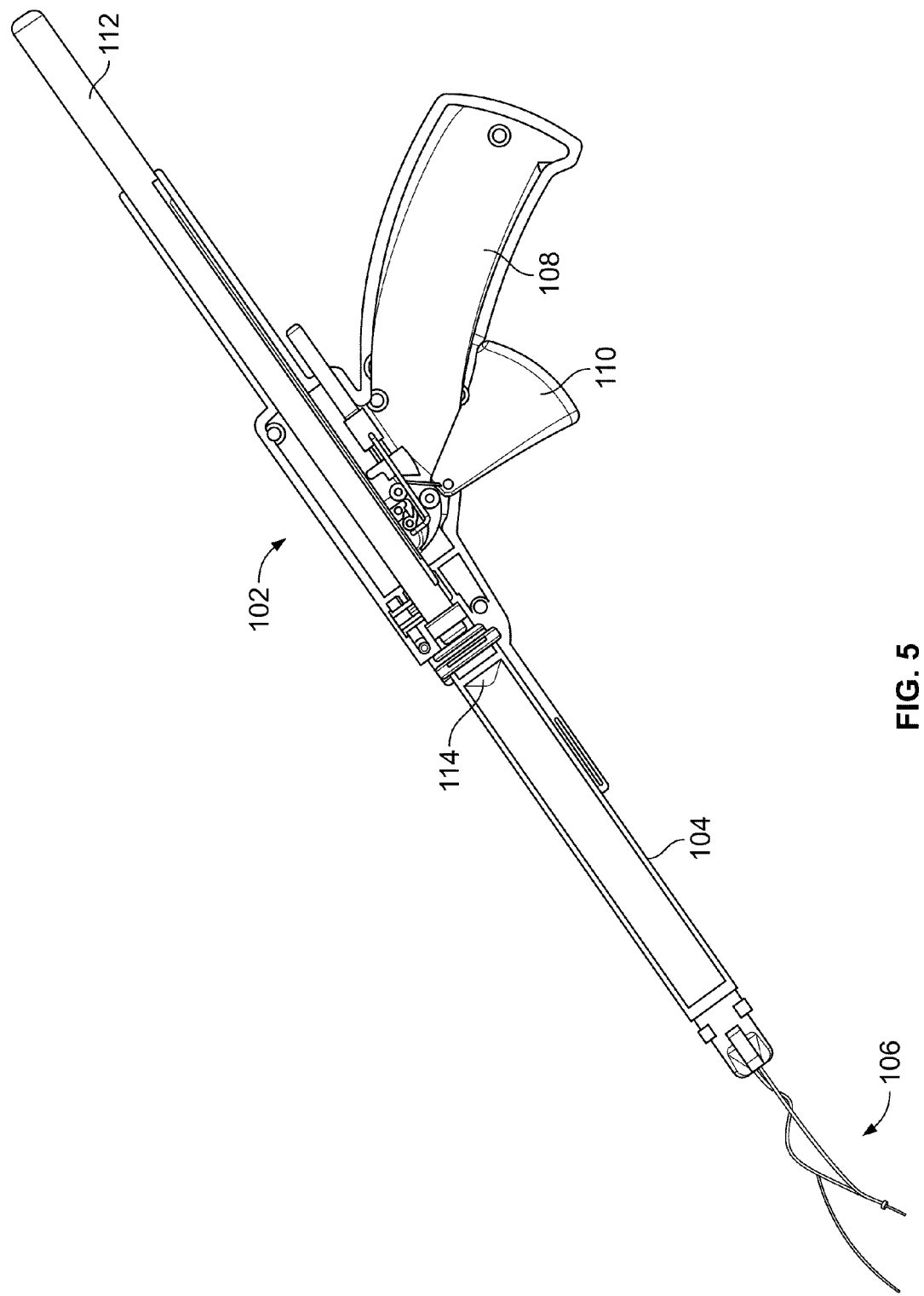
FIG. 5 is a partial cross-sectional view of an exemplary delivery device in accordance with some embodiments.

Referring to FIG. 5, delivery device 100 can include applicator portion 102. Delivery device 100 can be configured to maintain an adhesive cartridge (not shown) in cartridge housing 104. Cartridge housing 104 can be a hermetically-sealed, moisture free chamber that can be converted into a dispensing chamber at the time of use. In some embodiments, an adhesive cartridge can be pre-filled with viscous fluid and sealed at each end with a hermetically sealed barrier membrane. The barrier membrane seal can preserve the chemical composition of the viscous fluid (e.g., surgical adhesive) over a prolonged storage period. Cartridge housing 104 can engage delivery tip 106 such that attachment of delivery tip 106 to cartridge housing 104 when cartridge housing 104 contains a sealed adhesive cartridge can result in the breach of the barrier membrane seal on an adhesive cartridge. In another embodiment, delivery tip 106 can be rotated after attachment to cartridge housing 104 such that the rotation causes the breach of the barrier membrane seal on an adhesive cartridge. In some embodiments, applicator portion 102 can contain plunger 114 near the proximal end of cartridge housing 104 and set inside the barrier seal of an adhesive cartridge. When a user depresses actuator 110, push rod 112 applies pressure that can result in the breach of the barrier membrane seal on an adhesive cartridge. In such circumstances, push rod 112 can engage plunger 114 set inside the barrier membrane seal on the proximal end of the adhesive cartridge. As a result, the viscous fluid is advanced from cartridge housing 104 and to the distal end of delivery tip 106.

In some embodiments, cartridge housing 104 can engage delivery tip 106 such that attachment of delivery tip 106 to cartridge housing 104 when cartridge housing 104 contains a sealed adhesive cartridge does not result in the breach of the barrier membrane seal on an adhesive cartridge. In some embodiments, applicator portion 102 can contain plunger 114 near the proximal end of cartridge housing 104 and set outside the barrier seal of an adhesive cartridge. When a user depresses actuator 110, push rod 112 applies pressure that drives plunger 114 forward. The barrier membrane seals on both ends of the adhesive cartridge can be punctured upon forward movement of plunger 114. As a result, the viscous fluid is advanced from cartridge housing 104 and to the distal end of delivery tip 106. In some cases, an adhesive cartridge can contain plunger 114 located at the proximal end and set inside the barrier seal. In this case, when a user depresses actuator 110, push rod 112 can advance forward and engage plunger 114 located within the adhesive cartridge. As a result, subsequent actuation of actuator 110 can advance viscous fluid from cartridge housing 104 toward the distal end of delivery tip 106.

Any appropriate material can be used to make plunger 114. For example, plunger 114 may comprise a polymer material (e.g., rubber, PTFE, polypropylene with elastomeric seals, thermo-elastomeric resins, or fluorocarbon film coated onto molded elastomeric resin). Plunger 114 can be configured to withstand very high internal pressures generated during the dispensation process without leakage of the cartridge contents. Plunger 114 can slidably engage the interior wall of cartridge housing 104.

Figure 6:
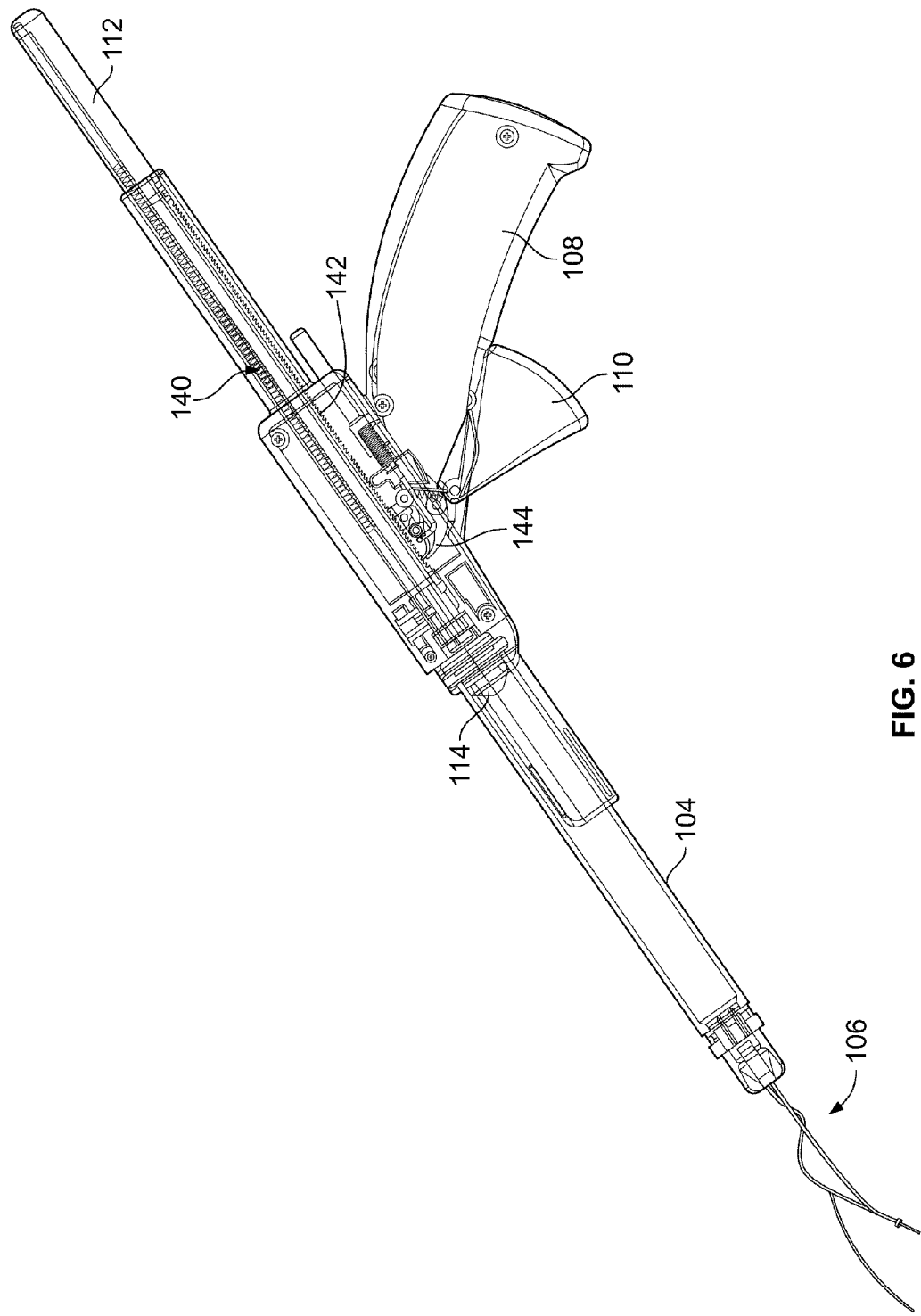
FIG. 6 is a cross-sectional view of the exemplary delivery device of FIG. 5.

Referring to FIG. 6, applicator portion 102 can include handle 108 and actuator 110. The user can apply force to actuator 110 in order to engage an internal actuator device. Any appropriate mechanism can be used to advance push rod 112 upon actuation of actuator 110. For example, a mechanical, hydraulic, or pneumatic mechanism can be used to advance push rod 112 upon actuation of actuator 110. The internal actuator device can include push rod 112, spring 140, ratchets 142 on push rod 112, and pawl mechanism 144. When the user depresses actuator 110, a cam surface molded to actuator 110 can apply a force to a forward advance pawl. The pawl can engage ratchets 142 mechanically attached or molded onto push rod 112. Ratchets 142 can be a machined or molded part. With each actuation, pawl mechanism 144 can advance forward by one increment of ratchet 142 such that push rod 112 is advanced by a predetermined amount, for example, between 0.5 and 5 mm (e.g., 1.15 mm). Once push rod 112 advances by the predetermined increment, a secondary pawl can engage ratchets 142 such that retraction is prevented. As push rod 112 advances, it can engage and advance plunger 114 by the same interval inside cartridge housing 104. The interval can be designed to dispense a precise volume of viscous fluid through delivery tip 106 upon each movement of the actuator. In some embodiments, the internal actuator device can include a mechanical "pull back" feature that pulls back pusher rod 112 following each forward advance. The pull back feature can permit plunger 114 to retreat and thereby reduce the pressure inside cartridge housing 104 following each discharge of viscous fluid. As described herein, viscous fluid to be dispensed from delivery device 100 can be in the form of a surgical adhesive. Some surgical adhesives can have a viscosity from about 200 cP to about 2,000 cP, about 500 cP to about 1500 cP, or about 500 cP to about 700 cP (measured at 25° C.). Particular formulations of the surgical adhesive may be moisture sensitive in that exposure to moisture (e.g., during dispensation onto the bodily tissue) causes a chemical process to initiate.

Referring to FIGS. 8-11, delivery device 200 can have applicator portion 202. Applicator portion 202 can be configured to engage cartridge housing 204 such that a push rod located within applicator portion 202 can be advanced into an adhesive cartridge 205 that is positioned within cartridge housing 204. Cartridge housing 204 can be configured to engage delivery tip 206 such that a viscous fluid maintained in adhesive cartridge 205 of cartridge housing 204 can be advanced to delivery tip 206. Applicator portion 202 can have handle 208, which can be configured to fit comfortably in a user's hand. Handle 208 can include actuator 210. Actuator 210 can be pushed or depressed by a user such that actuator 210 moves relative to a handle mechanism. In some cases, actuator 210 can be configured as a trigger, button, or other mechanism that can be moved by a user applying force using one or more fingers. The user can apply force to actuator 210 in order to engage an internal handle mechanism. The internal handle mechanism can be designed to advance push rod 212. Push rod 212 can be configured to engage plunger 214 in a manner that pushes and/or pulls plunger 214 inside adhesive cartridge 205 located with cartridge housing 204. Cartridge housing 204 can be configured to house adhesive cartridge 205 and to engage delivery tip 206 in a manner that allows a viscous fluid to move from adhesive cartridge 205 through channels or tubes of tip 206. Delivery tip 206 can have one or more supports 218 and brace 220. Brace 220 can have a generally cylindrical shape, a generally rectangular shape, or any other appropriate shape. Any appropriate material can be used to make actuator 210, handle 208, cartridge housing 204, delivery tip 206, supports 218, and brace 220. Such components can be made using, for example, plastic (e.g., polyethylene, high density polyethylene, polyvinyl chloride, polypropylene), metal (e.g., steel, titanium, aluminum), or glass (e.g., soda-lime glass, borosilicate glass, aluminosilicate glass).

Delivery device 200 can include delivery tip 206 mounted to the distal end of cartridge housing 204. Delivery tip 206 can be configured to include any appropriate number of supports (e.g., 1, 2, 3, 4, 5, 6, 7, 8, 9 or more supports) configured to support a tubular member for delivering a viscous fluid from an adhesive cartridge to a target site (e.g., skin lesion or surgical site). Supports 218 can have a generally cylindrical shape, a generally rectangular shape, or any other appropriate shape. Support 218 can include channel 222, which is configured to support a tubular member. Channel 222 can be, for example, a closed or open channel. In some cases, channels 222 can be configured to permit delivery of a viscous fluid in a dimensionally controlled repeatable pattern without the use of a tubular member. In some embodiments, supports 218 are of equal length. In such circumstances, drops of a highly viscous fluid that originate at the proximal ends of supports 218 will reach the distal end and delivery drops at the same time and at predetermined spacing. As demonstrated in FIGS. 8-11, one or more supports 218 can have a curved-shape or other non-linear shape in order to create supports of equal length. In some embodiments, brace 220 can separate supports 218 by a defined space. For example, supports 218 can be spaced between about 0.5 and 25 cm apart (e.g., about 0.5, 0.75, 1, 1.5, 2, 2.5, 3, 3.5, 4, 4.5, or 5 cm apart). The spacing of supports 218 of delivery tip 206 can permit a user to deliver a precise volume of a viscous fluid onto a surface (e.g., a planar surface) at predetermined positions equal to the number of supports. In some embodiments, delivery tip 206 can have three supports spaced about 2 cm apart in order to deliver three drops of a viscous fluid spaced about 2 cm apart on a planar surface.

Channels 222 can have tubular member 224. In some embodiments, tubular member 224 can have the same length as channel 222. In some embodiments, tubular member 224 can extend beyond the distal end of channel 222 and beyond brace 220. Tubular members 224 in each support 218 can be of equal lengths. In such circumstances, drops of a highly viscous fluid that originate at the proximal ends of tubular members 224 will reach the distal end and delivery drops at the same time and at positions pre-determined by the spacing of supports 218. Tubular member 224 can be made from any appropriate material. For example, tubular member 224 can be a flexible polymer material (e.g., polyimide, polyethylene, polypropylene, PTFE, or PTFE/FEP composite constructions). In some cases, a tubular member can be made of MicroLumen® medical tubing (MicroLumen, Tampa, Fla.). Tubular member 224 can have any appropriate inner diameter. For example, the inner diameter can be between 0.005 and 0.1 inches (e.g., between 0.005 and 0.05 inches, between 0.01 and 0.05 inches, between 0.02 and 0.05 inches, between 0.005 and 0.04 inches, or between 0.01 and 0.04 inches). In some cases, the inner diameter can be 0.0129 inches, 0.0151 inches, or 0.0299 inches. For example, the inner diameter can be 0.0152 inches to deliver 0.038 µL drops of adhesive when the adhesive viscosity is between about 500-2000 cP (e.g., 250, 400, 500, 750, 1000, 1250, 1500, 1750, or 2000 cP). Tubular member 224 can have any appropriate outer diameter. For example, the outer diameter can be between 0.01 and 0.5 inches (e.g., 0.021 inches, 0.023 inches, 0.025 inches). In some embodiments, tubular member 224 can have an outer diameter that is smaller than the inner diameter of channel 222. Upon actuation of delivery device 200, tubular member 224 can advance drops of a viscous fluid to the distal portion of delivery tip 206.

Delivery tip 206 can include spacing gauge 226. In some embodiments, spacing gauge 226 can extend from the midline of delivery tip 206 and extend beyond brace 220 by a predetermined length between about 0.5 and about 25 cm (e.g., 0.5, 1, 1.5, 2, 2.5, 3, 4, 5, 6, 7, 8, 9, 10, 11, 12, 13, 14, 15, 18, 20, 22, 23, 25 cm). In some cases, the distance of the distal tip of spacing gauge 226 from brace 220 can be equal or similar to the distance between the distal tips of tubular members 224. Any appropriate material can be used to make spacing gauge 226. For example, spacing gauge 226 can be made using plastic, metal, glass, or composite materials. In some embodiments, delivery tip 206 can have three supports spaced about 2 cm apart and one spacing gauge 226 positioned about 2 cm in front of or behind brace 220 in the same plane. In such circumstances, delivery device 200 can deliver three drops of a viscous fluid spaced about 2 cm apart on a surface (e.g., a planar surface). Also, spacing gauge 226 can be used to position the device to deliver another row of drops at a predetermined distance (e.g., 0.5, 1, 1.5, 2, 2.5 cm) in front of or behind the first row. The number of drops delivered per actuation can depend on the number of supports and tubular members of delivery tip 206. For example, delivery tip 206 with four supports 218 can deliver a row of four drops.

Cartridge housing 204 can be configured to engage delivery tip 206 by a positive engagement. The positive engagement can be, for example, a locking mechanism on the distal end of delivery tip 206. In some embodiments, a locking mechanism can be a Luer lock connector. Other appropriate locking mechanisms can include, for example, a custom designed cam locking system, a bayonet locking system, a screw thread with detent locking system, or permanent bonding and fixation of delivery tip 206. Delivery tip 206 can include hub 228 having a connecting portion and a housing portion. The housing portion of a hub can have any appropriate shape such as, for example, a generally rectangular box shape or a generally cylindrical shape. A generally rectangular box shape can have rounded edges. A connecting portion can be configured to engage cartridge housing 204 such that a channel is formed. The channel can be generally cylindrical or generally conical transitioning to a cylindrical shape. In some cases, the channel can be configured to narrow into an intermediate channel having a smaller diameter and generally cylindrical in shape. Such an intermediate channel can be configured to engage the proximal ends of tubular members 124 such that a viscous fluid can be advanced from adhesive cartridge 205 to the distal end of delivery tip 206.

Delivery device 200 can include applicator portion 202. Delivery device 200 can be configured to maintain adhesive cartridge 205 in cartridge housing 204. In some cases, cartridge housing 204 can be a hermetically-sealed, moisture free chamber that can be converted into a dispensing chamber at the time of use. In some embodiments, adhesive cartridge 205 can be pre-filled with viscous fluid and sealed at each end with a hermetically sealed barrier membrane. The barrier membrane seal can preserve the chemical composition of the viscous fluid (e.g., surgical adhesive) over a prolonged storage period. Cartridge housing 204 can engage delivery tip 206 such that attachment of delivery tip 206 to cartridge housing 204 when cartridge housing 204 contains a sealed adhesive cartridge can result in the breach of the barrier membrane seal on an adhesive cartridge. In another embodiment, delivery tip 206 can be rotated after attachment to cartridge housing 204 such that the rotation causes the breach of the barrier membrane seal on an adhesive cartridge. In some embodiments, applicator portion 202 can contain plunger 214 near the proximal end of cartridge housing 204 and set inside a barrier seal of an adhesive cartridge. When a user depresses actuator 210, push rod 212 applies pressure that can result in the breach of the barrier membrane seal on an adhesive cartridge. In such circumstances, push rod 212 can engage plunger 214 set inside the barrier membrane seal on the proximal end of the adhesive cartridge. As a result, the viscous fluid is advanced from cartridge housing 204 and to the distal end of delivery tip 206.

Figure 9:
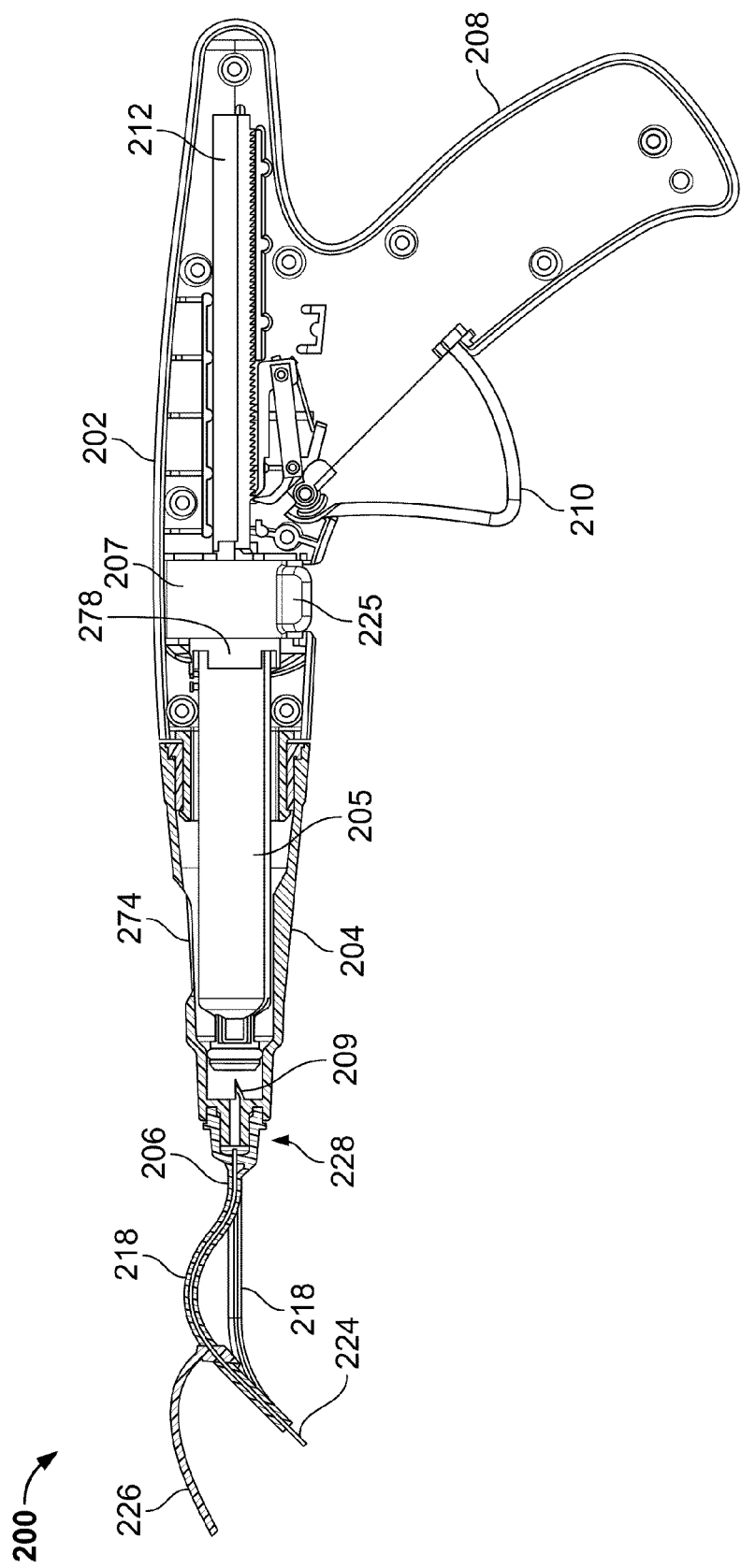
FIG. 9 is a partial cross-sectional view of the exemplary delivery device of FIG. 8.
Figure 10:
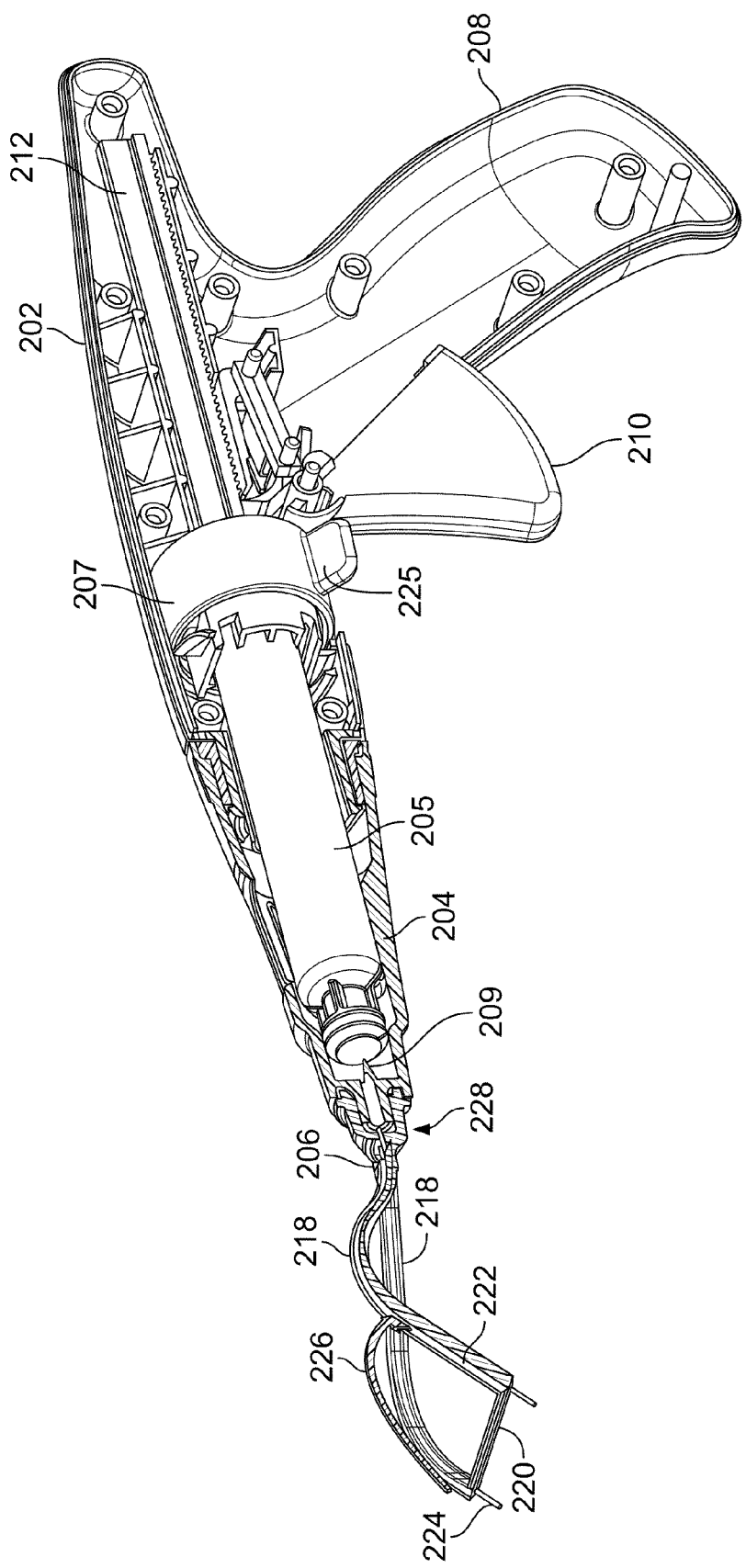
FIG. 10 is a front, side perspective view of a partial cross-section of the exemplary delivery device of FIG. 8.
Figure 11:
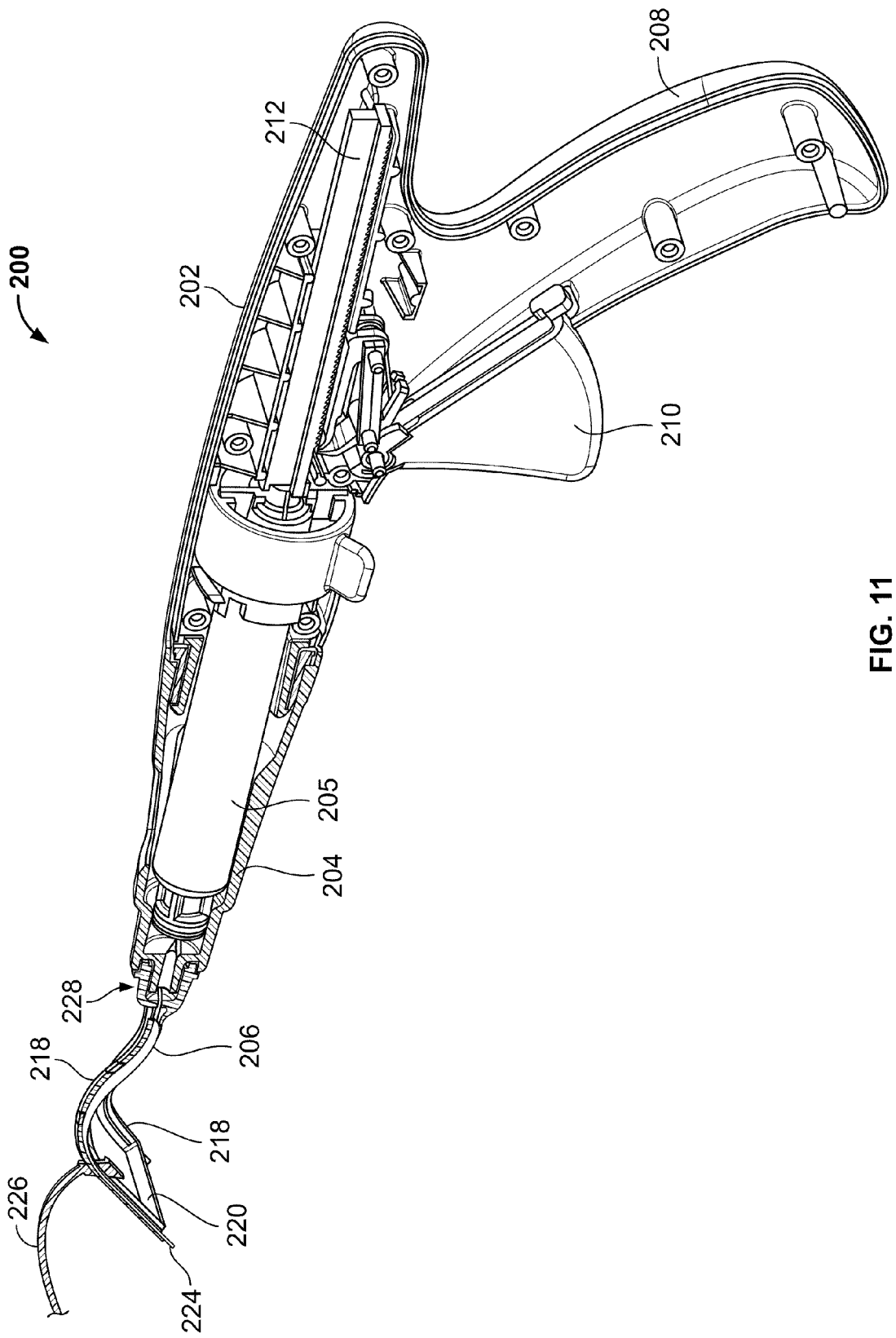
FIG. 11 is a rear, side perspective view of a partial cross-section of the exemplary delivery device of FIG. 8.

With reference to FIG. 9, applicator portion 202 can include actuator ring 207, and cartridge housing 204 can include piercing element 209. Actuator ring 207 can be configured to advance adhesive cartridge 205 forward towards the distal end of delivery device 200 within cartridge housing 204 as actuator ring 207 is actuated (e.g., rotated, switched, or moved). In some cases, actuation of actuator ring 207 can advance push rod 212 together with the advancement of adhesive cartridge 205 such that the distance between push rod 212 and adhesive cartridge 205 before and after actuation of actuator ring 207 is maintained. Such advancement of push rod 212 together with the advancement of adhesive cartridge 205 can limit or reduce the number of actuations of actuator 210 needed by a user to prime the device for delivering adhesive.

Figure 14:
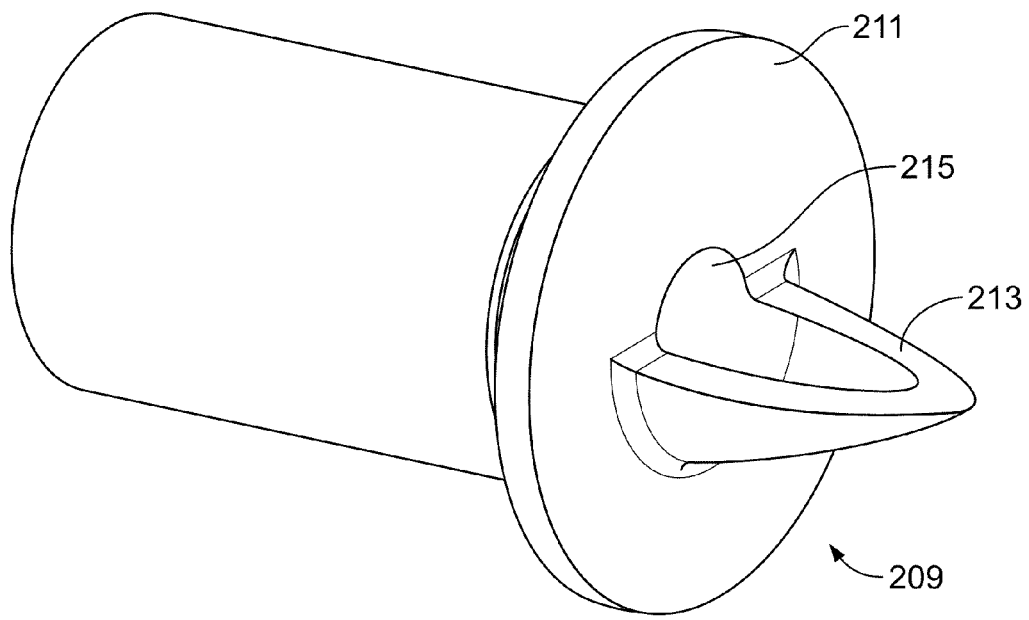
FIG. 14 is a front, side perspective view of a portion of a piercing element of an exemplary delivery device in accordance with some embodiments.
Figure 15:
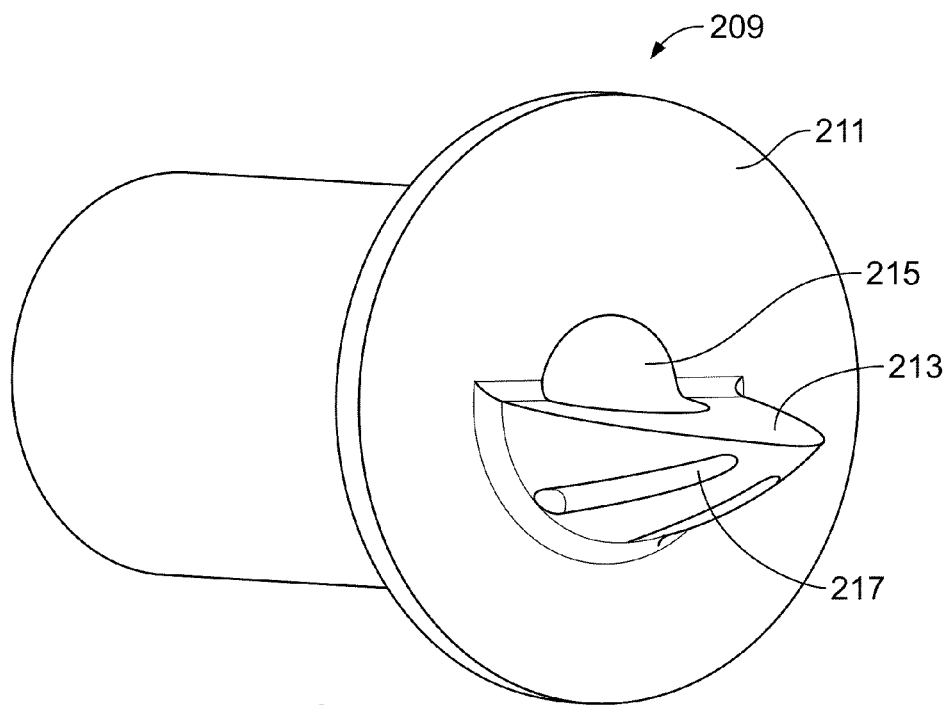
FIG. 15 is a front, side perspective view of a portion of a piercing element of an exemplary delivery device in accordance with some embodiments.

To aid in the rotation of actuator ring 207, actuator ring 207 can include grip 225. This advancement of adhesive cartridge 205 can result in breach of the barrier membrane seal on the distal end of adhesive cartridge 205 by virtue of piercing element 209. Piercing element 209 can be configured to have the ability to puncture the barrier membrane seal on the distal end of the adhesive cartridge by virtue of the movement of the adhesive cartridge in a distal direction. Piercing element 209 can define an opening such that the viscous fluid can advance through piercing element 209 from adhesive cartridge 205 to the distal end of delivery tip 206. With reference to FIG. 14, piercing element 209 can include base 211 and extension 213. Base 211 can define opening 215 such that the viscous fluid can advance through piercing element 209 from adhesive cartridge 205 to the distal end of delivery tip 206. Extension 213 can extend from base 211 and form a structure having the ability to puncture the barrier membrane seal (e.g., a foil seal) on the distal end of the adhesive cartridge by virtue of the movement of the adhesive cartridge in a distal direction. In some cases, extension 213 can be shaped to have a hollow cup shape as shown in FIG. 14. In some cases, extension 213 can include grooves 217 as shown in FIG. 15 to reduce the ability of the barrier membrane seal (e.g., a foil seal) of the adhesive cartridge, once pierced, from impeding flow of the viscous fluid through opening 215.

Figure 12:
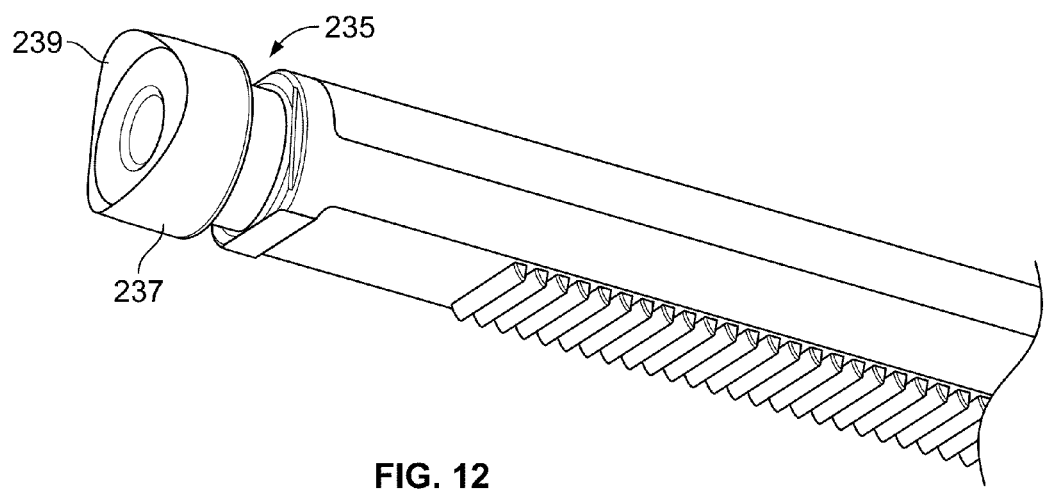
FIG. 12 is a perspective view of a portion of a push rod of an exemplary delivery device in accordance with some embodiments.
Figure 13:
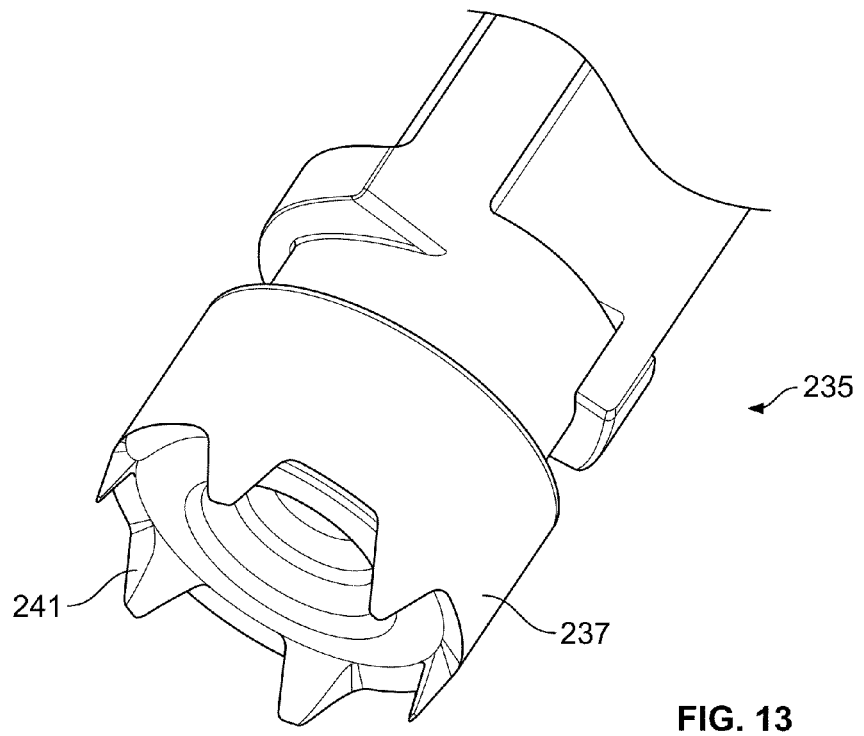
FIG. 13 is a perspective view of a portion of a push rod of an exemplary delivery device in accordance with some embodiments.

The distal end of push rod 212 can include seal piercing element 235 configured to breach the barrier membrane seal (e.g., a foil seal) on the proximal end of the adhesive cartridge by virtue of the forward movement of push rod 212 as trigger 210 is actuated. Seal piercing element 235 can include base 237 having one or more (e.g., two, three, four, five, six, or more) extensions. As shown in FIG. 12, seal piercing element 235 can include base 237 having extensions 239. In this case, extensions 239 are configured to form a sine wave shape. As shown in FIG. 13, seal piercing element 235 can include base 237 having extensions 241. In this case, extensions 241 are configured to form six equidistantly spaced extensions designed to puncture six locations around the parameter of the seal of the adhesive cartridge.

In some embodiments, cartridge housing 204 can engage delivery tip 206 such that attachment of delivery tip 206 to cartridge housing 204 when cartridge housing 204 contains a sealed adhesive cartridge does not result in the breach of the barrier membrane seal on an adhesive cartridge. In some embodiments, applicator portion 202 can contain plunger 214 near the proximal end of cartridge housing 204 and set outside the barrier seal of an adhesive cartridge. When a user depresses actuator 210, push rod 212 applies pressure that drives plunger 214 forward. The barrier membrane seals on both ends of the adhesive cartridge can be punctured upon forward movement of plunger 214. As a result, the viscous fluid is advanced from cartridge housing 204 and to the distal end of delivery tip 206. In some cases, an adhesive cartridge can contain plunger 214 located at the proximal end and set inside the barrier seal. In this case, when a user depresses actuator 210, push rod 212 can advance forward and engage plunger 214 located within the adhesive cartridge. As a result, subsequent actuation of actuator 210 can advance viscous fluid from cartridge housing 204 toward the distal end of delivery tip 206.

Any appropriate material can be used to make plunger 214. For example, plunger 214 may comprise a polymer material (e.g., rubber, PTFE, polypropylene with elastomeric seals, thermo-elastomeric resins, or fluorocarbon film coated onto molded elastomeric resin). Plunger 214 can be configured to withstand very high internal pressures generated during the dispensation process without leakage of the cartridge contents. Plunger 214 can slidably engage the interior wall of cartridge housing 204.

Referring to FIGS. 8-11, applicator portion 202 can include handle 206 and actuator 210. The user can apply force to actuator 210 in order to engage an internal actuator device. Any appropriate mechanism can be used to advance push rod 212 upon actuation of actuator 210. For example, a mechanical, hydraulic, or pneumatic mechanism can be used to advance push rod 212 upon actuation of actuator 210.

In some cases, the internal actuator device can include push rod 212, ratchets 245 on push rod 212, pawl mechanism 247, torsion spring 249, and arm 251 (see, e.g., FIGS. 8-11 and 18). When the user depresses actuator 210, a cam surface molded to actuator 210 can apply a force to a forward advance pawl (e.g., pawl mechanism 247). Pawl mechanism 247 can engage ratchets 245 mechanically attached or molded onto push rod 212. Ratchets 245 can be a machined or molded part. With each actuation, pawl mechanism 247 can advance forward by one increment of ratchet 245 such that push rod 212 is advanced by a predetermined amount, for example, between 0.5 and 5 mm (e.g., 1.15 mm). Once push rod 212 advances by the predetermined increment, arm 251 can engage ratchets 245 such that refraction is prevented. As push rod 212 advances, it can engage and advance plunger 214 by the same interval inside adhesive cartridge 205 within cartridge housing 204. The interval can be designed to dispense a precise volume of viscous fluid through delivery tip 206 upon each movement of the actuator.

Figure 16:
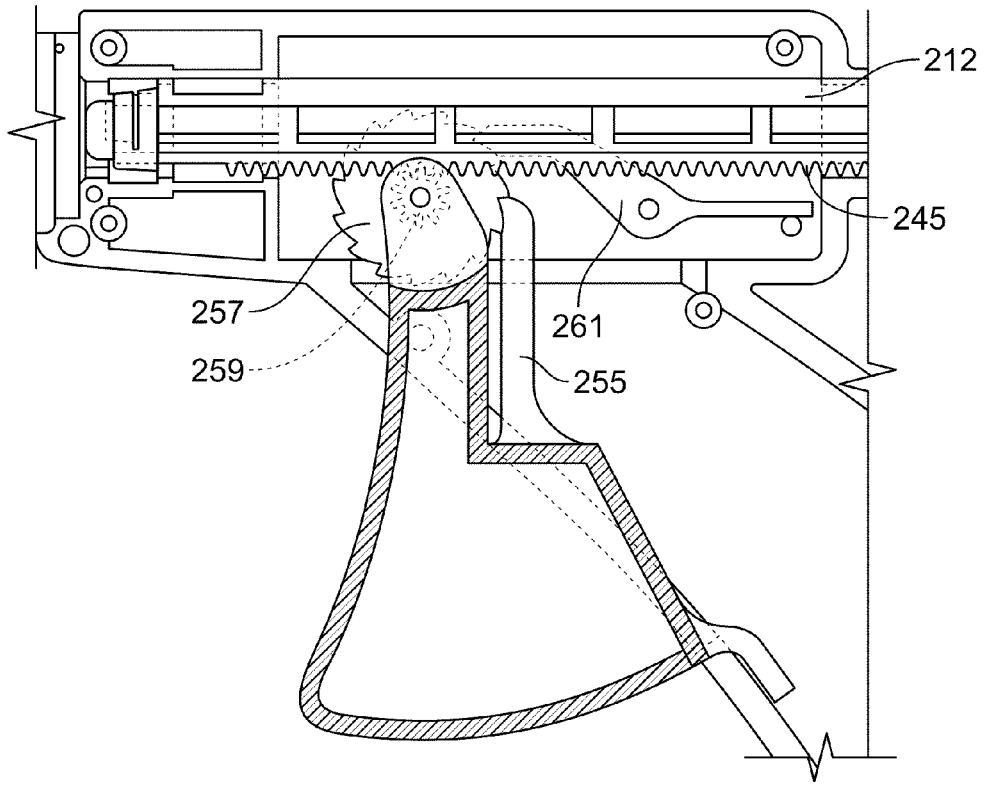
FIG. 16 is a cross-sectional view of a mechanical drive unit of an exemplary delivery device in accordance with some embodiments.

In some cases, the internal actuator device can have a rack and pinion design. For example, the internal actuator device can include push rod 212, ratchets 245 on push rod 212, advance arm 255, wheel 257, gear 259, and locking arm 261 (see, e.g., FIG. 16). When the user depresses actuator 210, actuator 210 can apply a force to advance arm 255 such that advance arm 255 causes advance wheel 257 and gear 259, which rotates with wheel 257 and is engaged with ratchets 245, to rotate. Rotation of gear 259 causes pusher rod 212 to advance, and locking arm 261 is configured to prevent the reverse movement of pusher rod 212 by virtue of its engagement with wheel 257. Ratchets 245 can be mechanically attached or molded onto push rod 212. Ratchets 245 can be a machined or molded part. With each actuation, the internal actuator device can advance forward by one increment (or a set of increments) of ratchet 245 such that push rod 212 is advanced by a predetermined amount, for example, between 0.5 and 5 mm (e.g., 1.15 mm). As push rod 212 advances, it can engage and advance plunger 214 by the same interval inside adhesive cartridge 205 within cartridge housing 204. The interval can be designed to dispense a precise volume of viscous fluid through delivery tip 206 upon each movement of the actuator.

Figure 17:
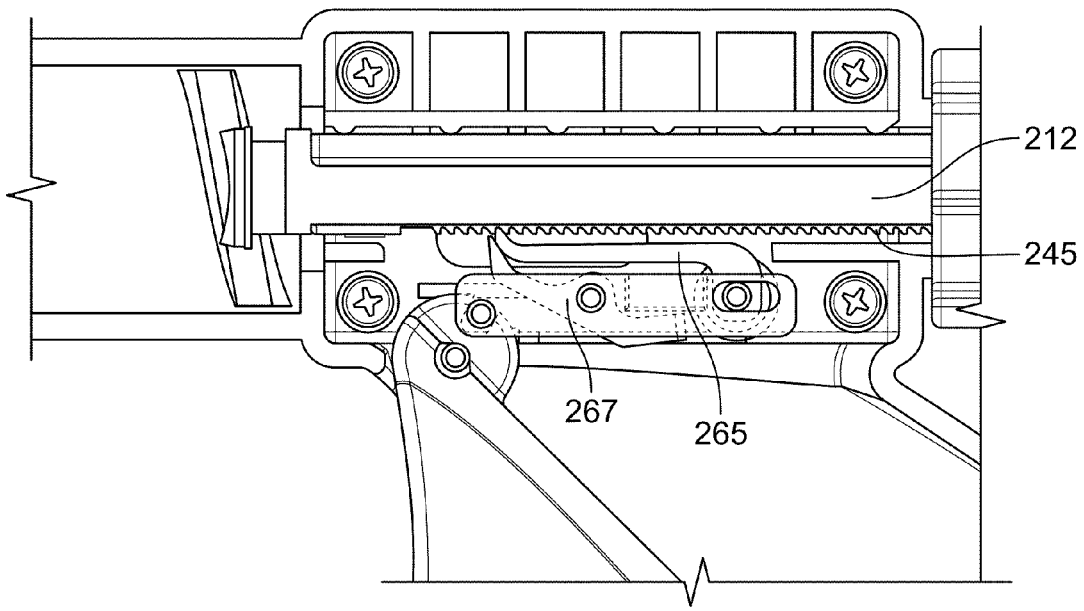
FIG. 17 is a cross-sectional view of a mechanical drive unit (e.g., sliding ratchet) of an exemplary delivery device in accordance with some embodiments.
Figure 18:
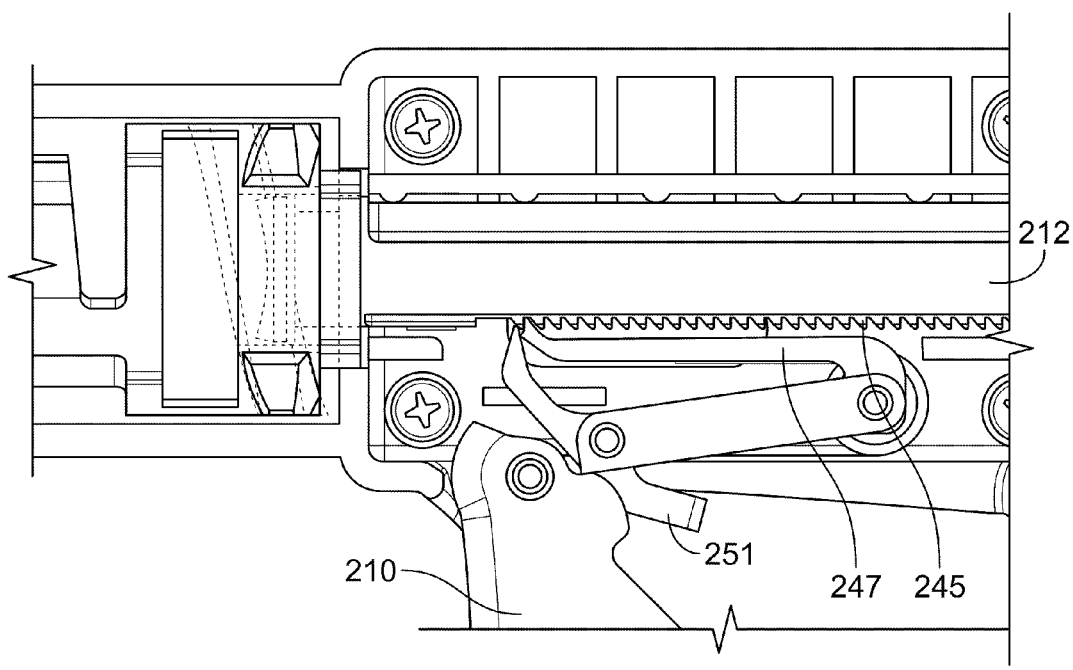
FIG. 18 is a cross-sectional view of a mechanical drive unit of the exemplary delivery device of FIG. 8.

In some cases, the internal actuator device can have a three pivot ratchet design. For example, the internal actuator device can include push rod 212, ratchets 245 on push rod 212, advance arm 265 and locking arm 267 (see, e.g., FIG. 17). When the user depresses the actuator 210, actuator 210 can apply force to the linkage 267. The actuator 210 can apply force axially to linkage 267, therefore transferring motion into the pawl mechanism 247. In some cases, pins attached to linkage 267 can be guided by channels within the housing to ensure axial travel only. Linkage 267 can move parallel with push rod 212. With each actuation of actuator 210, pawl mechanism 247 can advance forward one increment of ratchet 245.

In some embodiments, the internal actuator device can include a mechanical "pull back" feature that pulls back pusher rod 212 following each forward advance. The pull back feature can permit plunger 214 to retreat and thereby reduce the pressure inside cartridge housing 204 following each discharge of viscous fluid. As described herein, viscous fluid to be dispensed from delivery device 200 can be in the form of a surgical adhesive. Some surgical adhesives can have a viscosity from about 200 cP to about 2,000 cP, about 500 cP to about 1500 cP, or about 500 cP to about 700 cP (measured at 25° C.). Particular formulations of the surgical adhesive may be moisture sensitive in that exposure to moisture (e.g., during dispensation onto the bodily tissue) causes a chemical process to initiate.

With further reference to FIGS. 8-11, adhesive cartridge 205 can include O-ring 270. O-ring 270 can be configured to allow adhesive cartridge 205 to slide forward as actuator ring 207 is rotated and to restrict flow of viscous fluid from adhesive cartridge 205 past O-ring 270 towards the proximal end of delivery device 200. In some cases, plunger 214 can include O-rings 272. O-rings 272 can be configured to maintain viscous fluid in front of plunger 214 as plunger 214 is advanced toward the distal end of delivery device 200. In some cases, delivery device 200 can include window 274. Window 274 can be constructed of transparent material (e.g., polypropylene, cyclo-olefin polymers, or polycarbonate) such that the user can observe the inside of adhesive cartridge 205. In such cases, adhesive cartridge 205 also can be constructed of clear material. In some cases, cartridge housing 204 can define an opening in place of or in addition window 274. Like window 274, the opening can be configured such that the user can observe the inside of adhesive cartridge 205. In some cases, delivery device 200 can include snap ring 276 located between cartridge housing 204 and applicator portion 202. Snap ring 276 can be ultrasonically welded to cartridge housing 204 since, in some cases, it cannot be molded into the cartridge housing itself. Snap ring 276 can be configured to enable cartridge housing 204 to snap onto the distal end of applicator portion 202. Snap ring 276 can be involved in assembly, thereby allowing the cartridge to be placed within cartridge housing 204 and snapped onto applicator portion 202.

Figure 22:
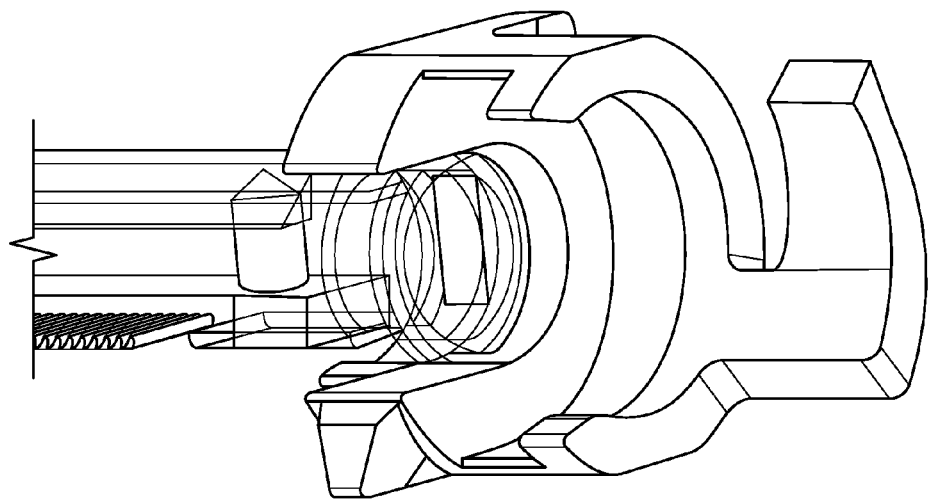
FIG. 22 is an enlarged view of an exemplary push rod captured by an exemplary shipping key.
Figure 23:
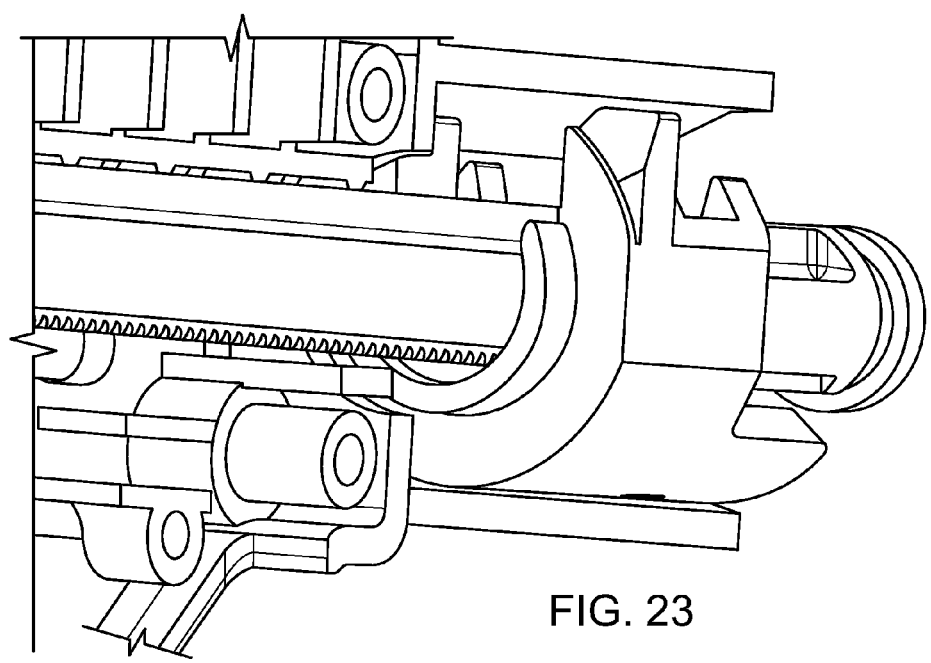
FIG. 23 is an enlarged view of an exemplary shipping key rotated to an unlocked position. In this case, the exemplary push rod can pass freely over the shipping key, which can allow it to enter cartridge and engage a plunger.
Figure 24:
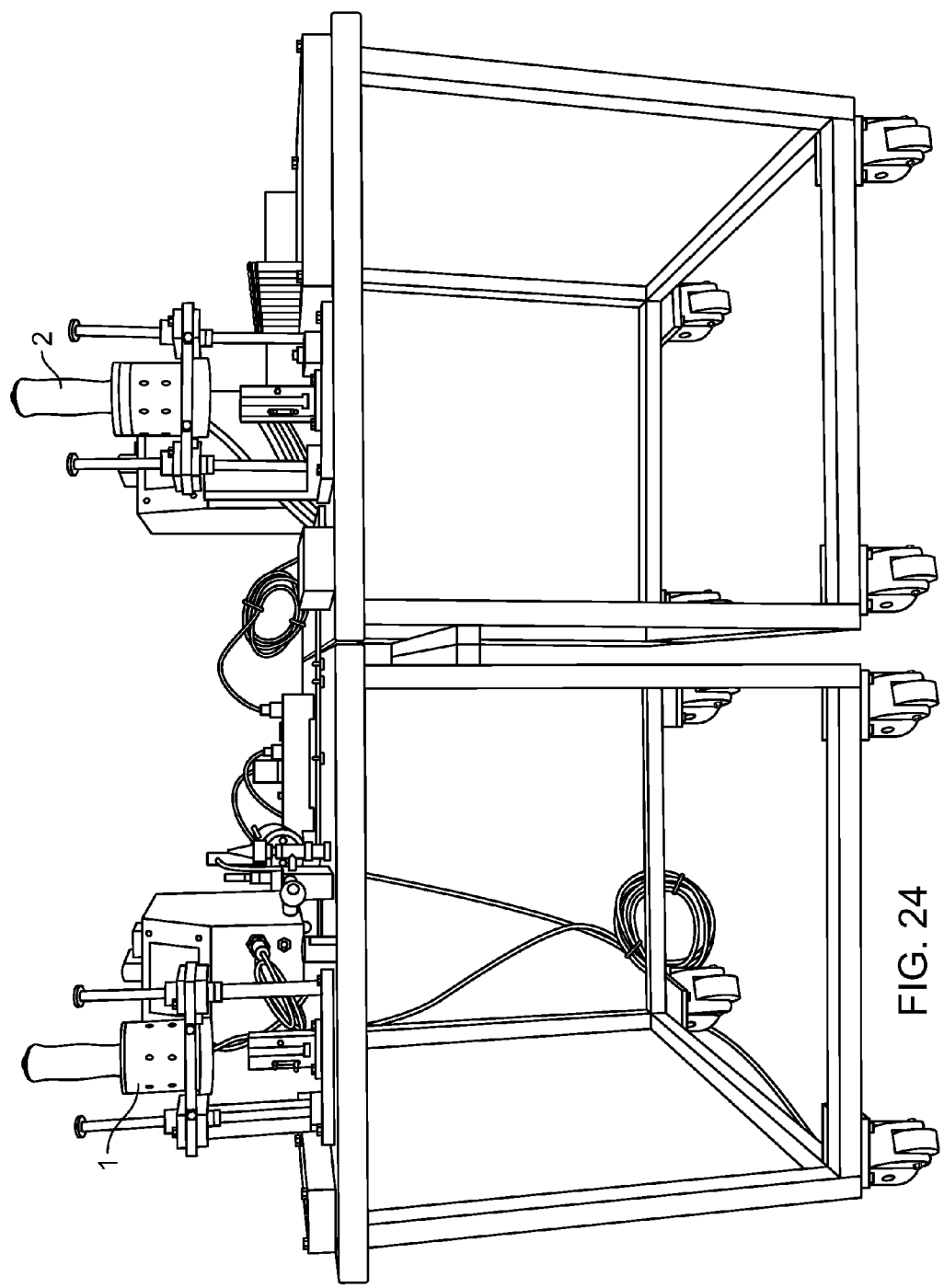
FIG. 24 is a front view photograph of exemplary distal and proximal sealing stations. Item 1, distal sealing station on a movable cart; and item 2, proximal sealing station on movable cart.
Figure 25:
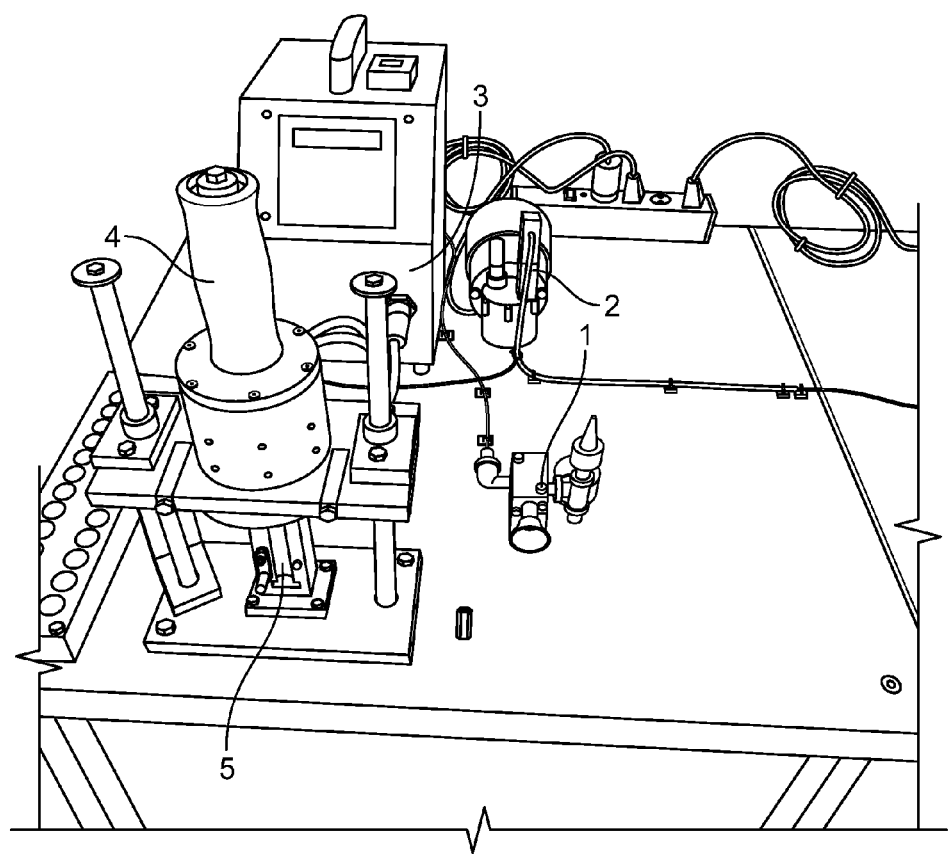
FIG. 25 is an enlarged, front view photograph of the exemplary distal sealing station of FIG. 24. Item 1, seal test fixture (a cartridge is placed over nozzle and pressurized); item 2, vacuum pump for sealing heads; item 3, power unit for induction seal head; item 4, induction seal head; and item 5, fixture to hold cartridge in place during sealing process.
Figure 26:
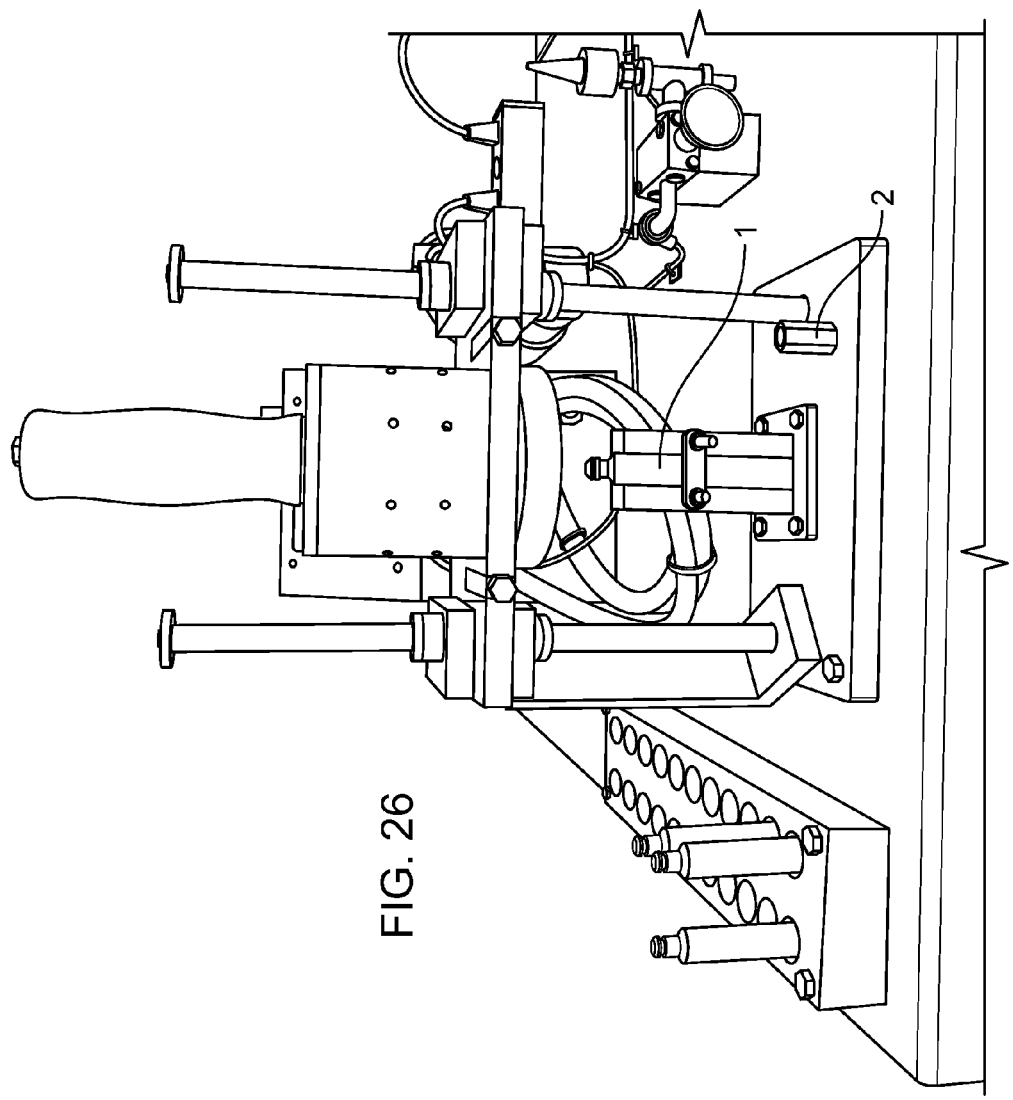
FIG. 26 is an enlarged, front view photograph of the exemplary distal sealing station of FIG. 24. Item 1, cartridge in sealing fixture; and item 2, fixture to place seal in sealing head.
Figure 27:
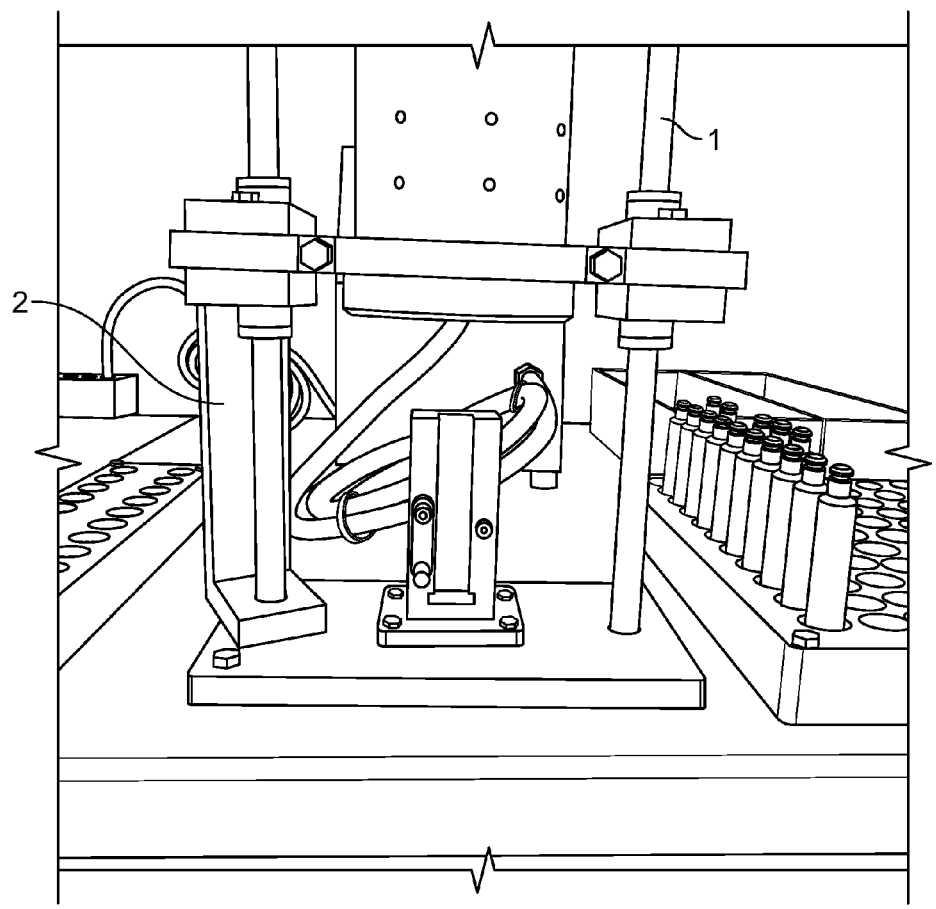
FIG. 27 is an enlarged, front view photograph of the exemplary proximal sealing station of FIG. 24. Item 1, guides for sealing head axial travel; and item 2, fixture to stabilize head during seal placement onto cartridge.

In some cases, delivery device 200 can include shipping key 278 located distally of actuator ring 207 (see, e.g., FIGS. 22 and 23). Shipping key 278 can be configured to hold the rack during actuation of the actuator ring. As the actuator ring is rotated, the cartridge can move forward axially and is pierced at the distal end of the cartridge. The shipping key can be attached to the push rod and can keep the distance between the proximal seal and push rod equal throughout the puncturing of the distal seal to minimize the number of actuations required to prime the device.

In some embodiments, a suitable adhesive can include the reaction product of: (a) an isocyanate component having an average functionality of at least 2; (b) an active hydrogen component having an average functionality greater than 2.1; and (c) an ionic salt component having an average hydroxyl or amino functionality, or combination thereof, of at least 1. In some embodiments, delivery device 100 can be configured to store the adhesive for a storage life of about 6 months to about 24 months (e.g., 6, 8, 10, 12, 14, 16, 18, 20, 22, or 24 months). Upon application of the surgical adhesive to biological tissue in the presence of moisture, the adhesive can crosslink to form a polymer network. The crosslinked network can biodegrade over time, thereby permitting the closed incision to fully heal and the polymer to be fully absorbed by the body.

The isocyanate component can have an average isocyanate functionality of at least 2, and can be at least 3. The term "average" reflects the fact that the multi-functional isocyanate component can include multiple types of isocyanates, including isocyanates with different functionalities. Suitable isocyanates are hydrophilic, and include those derived from amino acids and amino acid derivatives. Specific examples include lysine di-isocyanate ("LDI") and derivatives thereof (e.g., alkyl esters such as methyl or ethyl esters) and lysine tri-isocyanate ("LTI") and derivatives thereof (e.g., alkyl esters such as methyl or ethyl esters). Dipeptide derivatives also can be used. For example, lysine can be combined in a dipeptide with another amino acid (e.g., valine or glycine).

The active hydrogen component includes one or more active hydrogen reactants. The component can have an average functionality greater than 2.1. Again, the term "average" reflects the fact that the active hydrogen component can include multiple types of active hydrogen reactants, including reactants with different functionalities. Some or all of the active hydrogen reactants can have an equivalent weight less than 100. The term "equivalent weight" refers to molecular weight divided by functionality. Thus, for example, glycerol, which has a molecular weight of 92 and a hydroxyl functionality "f" of 3, has an equivalent weight of about 31. Examples of suitable active hydrogen components include, without limitation, hydroxyl-functional components, amine-functional components, thiol-functional components, carboxylic acid-functional components, and combinations thereof. In some embodiments, some or all of the functional groups can be primary groups. One class of suitable active hydrogen components includes multi-functional alcohols selected from glycerol, di-glycerol, erythritol, pentaerythritol, xylitol, arabitol, fucitol, ribitol, sorbitol, mannitol, and combinations thereof. Also suitable are hydroxyalkyl derivatives and esters of any of these alcohols such as ethoxylated pentaerythritol. Another class of suitable active hydrogen components includes hydroxyalkyl derivatives of C3-C10 carboxylic or dicarboxylic acids (e.g., dimethylol propionic acid, dimethylol butyric acid, and combinations thereof), and hydroxyalkyl derivatives of C3-C10 hydrocarbons (e.g., trimethylol propane). The active hydrogen component can also be a hydroxyalkyl amine (e.g., triethanolamine), a di-, tri-, or tetralkylene glycol, or combination thereof. Also suitable are hydroxyl-functional compounds selected from saccharides (e.g., glucose, fructose, sucrose, or lactose), oligosaccharides, polysaccharides, esters thereof, and combinations thereof.

The ionic salt includes one or more hydroxyl and/or amino functional groups. Consequently, it is able to react with the isocyanate-functional component of the reaction mixture, and thereby become covalently incorporated in the adhesive. Examples of suitable salts include, without limitation, ammoniates, halides, sulfonates, phosphonates, carboxylates, and combinations thereof. Specific examples include ammonium halides (e.g., ethyl triethanol ammonium chloride), choline halides (e.g., choline chloride), and combinations thereof.

In some embodiments, the adhesive can further include a catalyst. Examples of suitable catalysts include, without limitation, tertiary amines (e.g., aliphatic tertiary amines) and organometallic compounds (e.g., bismuth salts and zirconium chelates). Specific examples include 1,4-diazabicyclo[2.2.2]octane ("DABCO"), 2,2'dimorpholine diethyl ether ("DMDEE"), dibutyltin dilaurate ("DBTDL"), bismuth 2-ethylhexanoate, and combinations thereof. The amount of catalyst is selected based upon the particular reactants.

In some embodiments, the adhesive can include a rheology modifying agent in the form of a solvent, a non-volatile diluent, and/or a volatile diluent. Examples of suitable solvents include dimethylsulfoxide (DMSO), dimethylformamide (DMF), tetrahydrofuran (THF), glyme, and combinations thereof. Examples of suitable non-volatile diluents include dimethylsulfoxide (DMSO), propylene carbonate, diglyme, polyethylene glycol diacetates, polyethylene glycol dicarbonates, dimethylisosorbide, and combinations thereof. Examples of suitable volatile diluents include hydrocarbons, hydrofluoroalkanes, carbon dioxide, and combinations thereof. A single reagent can perform multiple roles. Thus, for example, DMSO can function as both a solvent and a non-volatile diluent. The amount of the rheology modifying agent is selected based upon the constituents of the adhesive and the particular application for which the adhesive is being used.

Moreover, in some embodiments, the adhesive may also include one or more stabilizers. Examples include antioxidants (e.g., BHT and BHA), water scavengers (e.g., acyl and aryl halides, and anhydrides), Bronsted acids, and the like.

In some embodiments, the delivery devices provided herein (e.g., delivery devices 100 and 200) can be configured to dispense a viscous fluid in the form of an adhesive. For example, delivery devices 100 and 200 can be used to deliver the surgical adhesive to a targeted tissue area of a patient's body during a medical procedure (e.g., abdominoplasty). In such circumstances, the viscous fluid can comprise a surgical adhesive that is delivered to a targeted tissue site for purposes of at least partially closing an incision, a wound, or other opening in bodily tissue. In some embodiments, the medical procedure can be an abdominoplasty procedure in which an area of skin in the patient's mid-region receives the surgical adhesive. For instance, the surgical adhesive can be applied to the targeted tissue area along the underside of a portion of skin proximate an opening so as to adhere the layer of skin tissue to the underlying tissue. In this particular example of the abdominoplasty procedure, the surgical adhesive can be applied to the targeted tissue area after the surgeon has used a scalpel or other instrument to at least partially remove excess skin from the patient's mid-region. The underside of the skin can be exposed so that drops of surgical adhesive can be deposited to the targeted tissue area. Thereafter, the skin layer can be adhered to the underlying tissue while the incision optionally is closed using wound closure techniques such as staples or sutures along the incision.

Figure 19:
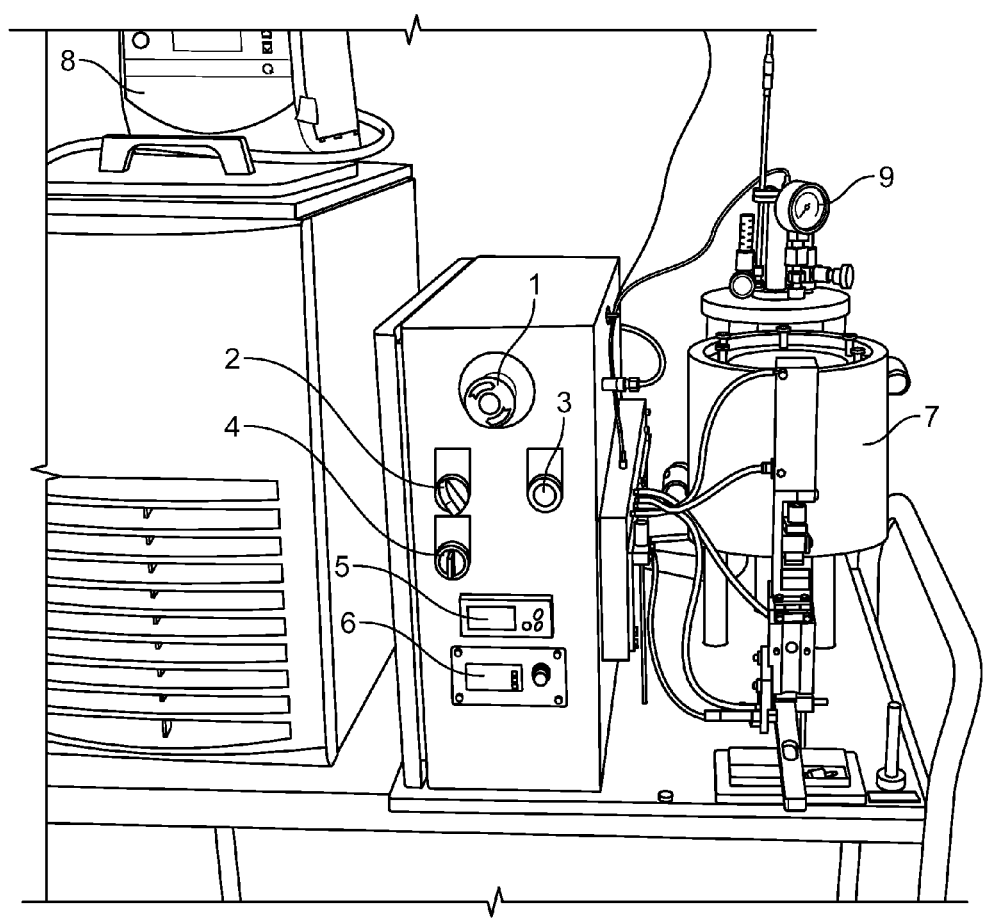
FIG. 19 is a front view photograph of an exemplary filling station. The fluid or flow path is not shown as it can be disposable and removed from the system between uses. Item 1, emergency stop; item 2, power—on/off; item 3, cycle start button; item 4, pinch valve override; item 5, product in vessel temperature readout; item 6, product in vessel height sensor (e.g., sonar); item 7, double walled chilled vessel (e.g., 1 Liter); item 8, chiller (e.g., Fisher Scientific chiller); and item 9, nitrogen pressure gauge (target pressure between 30 and 50 psi (e.g., 40 psi)).
Figure 20:
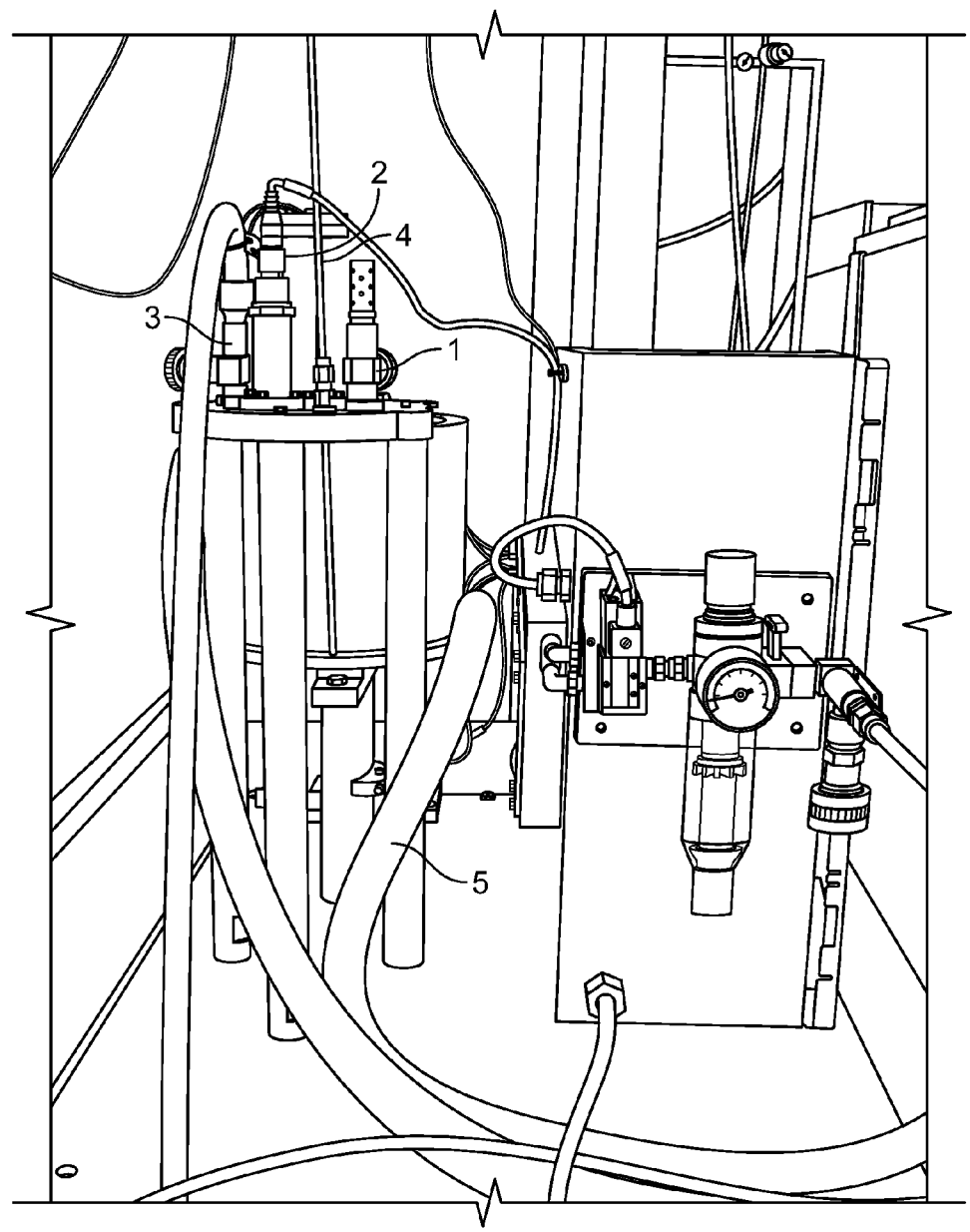
FIG. 20 is a rear view photograph of the exemplary filling station of FIG. 19. Item 1, nitrogen bleed off valve; item 2, product height sensor (e.g., sonar); item 3, nitrogen line; item 4, thermocouple; and item 5, supply line for chilling fluid.
Figure 21:
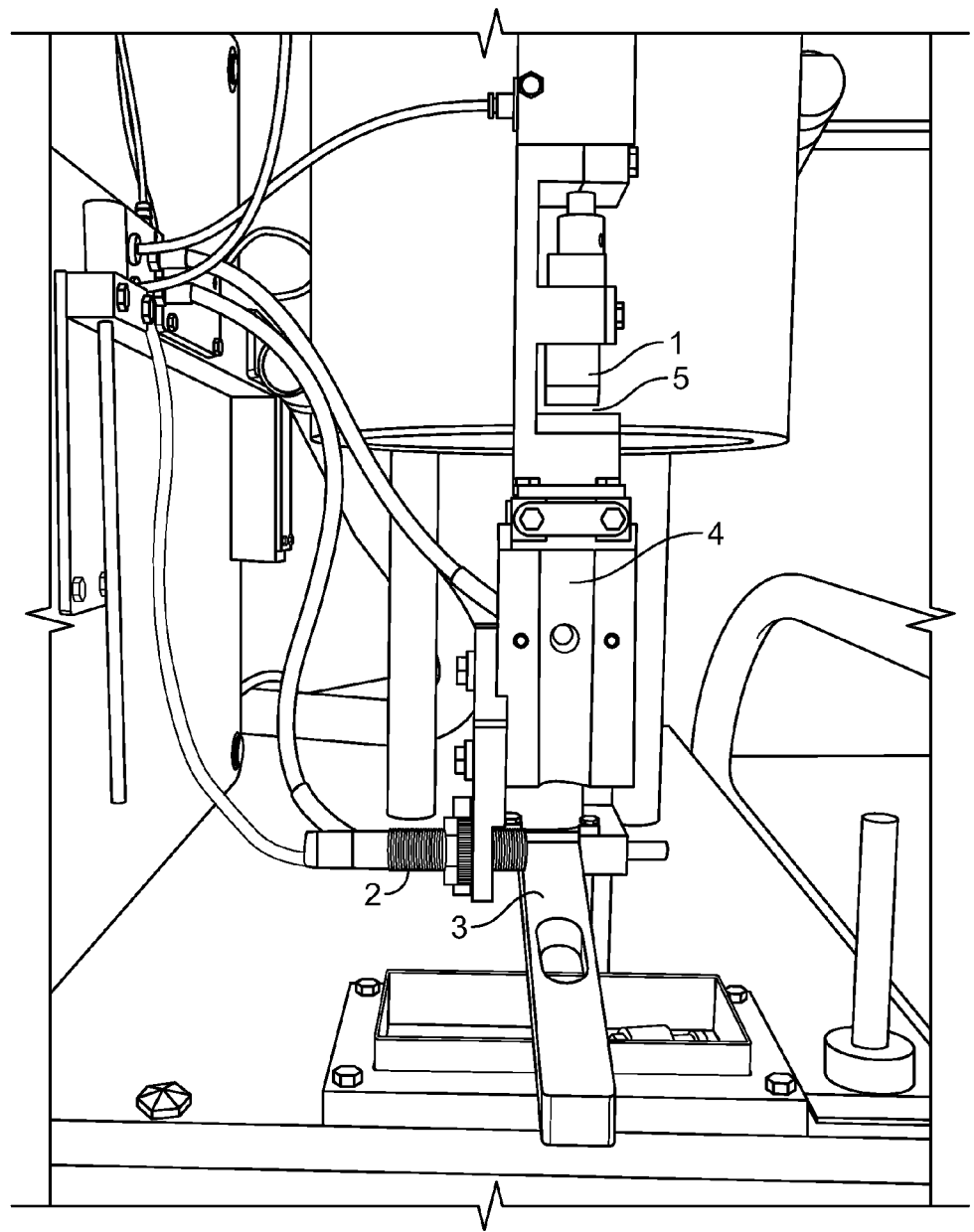
FIG. 21 is an enlarged, front view photograph of a portion of the exemplary filling station of FIG. 19. Item 1, pinch valve; item 2, proximity switch (e.g., to shut off flow when plunger inside cartridge passes); item 3, cartridge placement fixture; item 4, filling nozzle location (nozzle not present); and item 5, space for a portion of the flow path (e.g., silicone tubing (not shown)).

Any appropriate method can be used to fill an adhesive cartridge with a viscous fluid (e.g., a viscous adhesive). For example, a manual table top filling station can be used to fill an adhesive cartridge with a viscous fluid. The table top manual filling station can include a product surge vessel/tempered water system (see, e.g., FIGS. 19-21). The viscous fluid product for filling can be provided by the product surge vessel, which can have a capacity of about 0.5, 1.0, 1.5, or more liters. The product surge vessel can include a jacket that receives temperature controlled re-circulated cooling fluid from a refrigerated bath (e.g., a Thermo Scientific refrigerated bath) to maintain product temperature. The temperature of the product can be maintained between −15° C. and 15° C. (e.g., between −15° C. and 10° C., −15° C. and 5° C., −10° C. and 10° C., −10° C. and 0° C., −5° C. and 0° C., or about −2° C.). In some cases, the temperature of the product can be maintained below 5° C. Regulated nitrogen can be provided to the product surge vessel to provide the pressure for filling. Nitrogen can be used to pressurize the vessel because it has the ability to limit the condensation that may build within the product surge vessel (which can be chilled to about −2° C.). Such condensation can have an adverse effect on the product integrity. The pressure can be between 30 and 50 psi (e.g., between 30 and 45 psi, between 35 and 50 psi, between 35 and 45 psi, or about 40 psi).

The viscous fluid product can flow from a stainless steel product surge vessel into a polypropylene cartridge by means of a controlled product path. To reduce agitation of the adhesive and increase time until cartridge head space is compromised, the product can flow through a single diameter with limited distortion. As the product heats, its volume can increase, thereby causing the product to flow over the cartridge face, which may prevent an adequate seal. The product flow path can include an exit orifice from the product surge tank, a silicone tube, and a fill nozzle that is perpendicular to the base plane. In some cases, the silicone tubing may not be chilled. In such cases, its length can be kept to a minimum to reduce the effect ambient air has on product temperature as the product flows from the product surge vessel to the cartridge. While sitting on axis with the table top manual filling station, an operator can place the cartridge to be filled into a distal receiving station and secure the cartridge using a cartridge holder. In some cases, the cartridge holder can be verified as being correctly engaged. The presence of the cartridge can be verified to prevent accidental activation of product flow. The operator can activate the fill cycle, which can result in the release of a valve (e.g., a pinch valve), thereby allowing the discharge of product into the cartridge via pressure. As the cartridge is filled, a stopper can be displaced, thereby travelling towards the proximal end of the cartridge. Once the stopper reaches a stopper height sensor, the valve (e.g., the pinch valve) can automatically close, thereby stopping the flow of product. At this point, the operator can remove the filled cartridge and immediately place it into a distal end sealing station.

In some cases, a table top manual filling station can include one or more control elements. For example, the filling station can include a control element configured to allow the equipment to be powered on, a control element configured to allow the filling cycle to be activated, and a control element configured to provide an emergency stop. In some cases, a table top manual filling station can include one or more sensors. For example, the filling station can include a temperature sensor configured to provide temperature information about the product in the product surge vessel, a level sensor configured to provide information about the level of product with the cartridge or product surge vessel, or a pressure sensor configured to provide information about the pressure within the product surge vessel. In some cases, the filling station can include an electrical enclosure to house at least some of the electrical components of the control elements or sensors.

A table top manual sealing station can be used to seal the distal and proximal ends of the cartridge once the cartridge is filled (see, e.g., FIGS. 24-27). In some cases, the seal can be a foil seal. Sitting on axis with a table top manual sealing station, an operator can place sealing foil onto the underside of a distal sealing head. In some cases, the sealing foil can be held in place via a vacuum. The operator can insert the filled cartridge into a distal receiving station and secure the cartridge. At this point, the distal sealing head can be lowered so that the foil is induction sealed onto the cartridge. Time and energy controllers can be used to set the time and energy used to create the induction seal.

Once the distal end is sealed, an operator can place a sealing foil onto the underside of a proximal sealing head. In some cases, the sealing foil can be held in place via a vacuum. The operator can insert the distal end sealed cartridge into a proximal receiving station and secure the cartridge. At this point, the proximal sealing head can be lowered so that the foil is induction sealed onto the cartridge. Time and energy controllers can be used to set the time and energy used to create the induction seal. Once the sealing cycle is completed, the operator can remove the cartridge from the proximal sealing station and visually inspects the cartridge for completeness.

Figure 7:
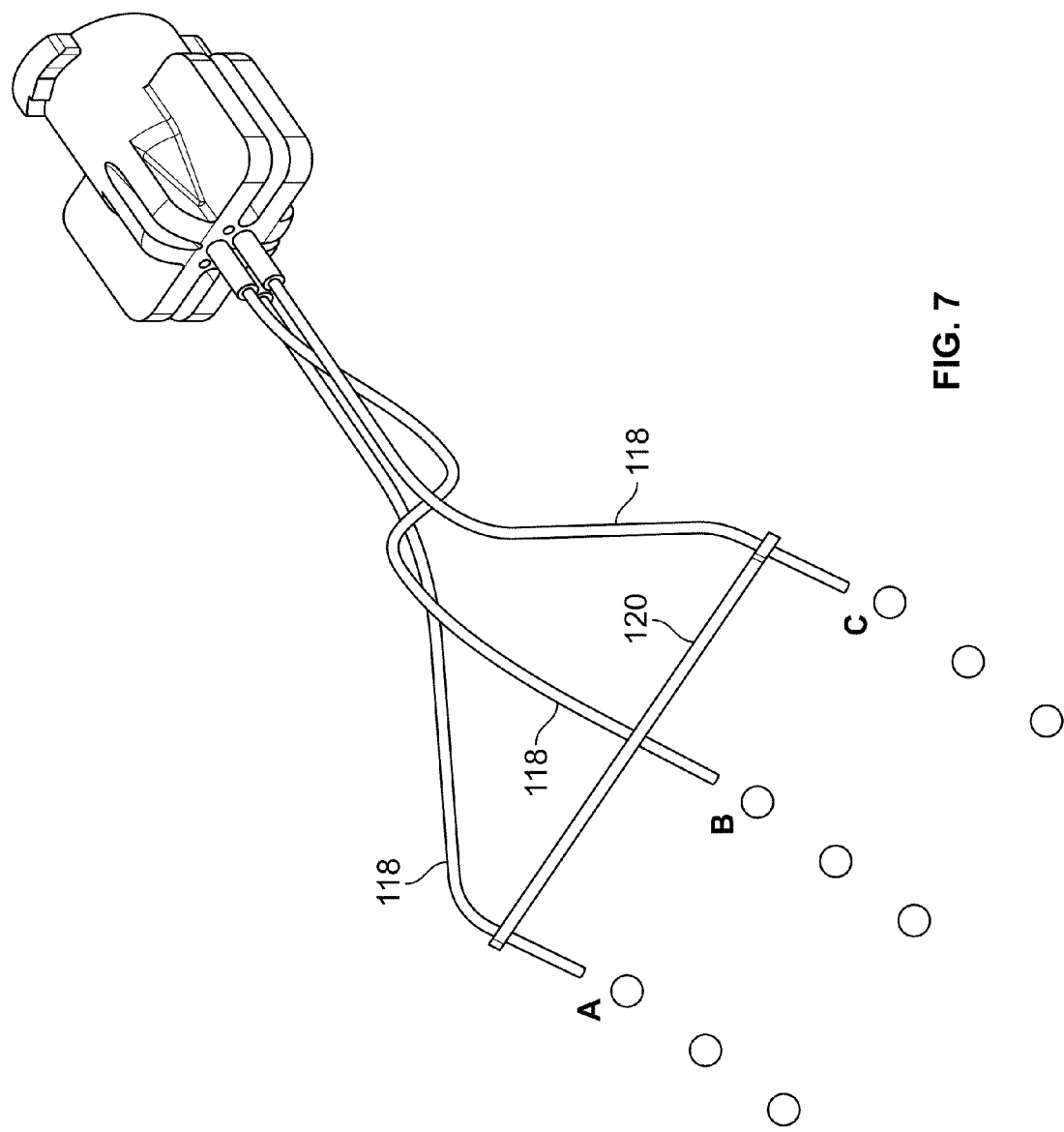
FIG. 7 is an enlarged perspective view of a portion of an exemplary delivery device in accordance with some embodiments.
Figure 8:
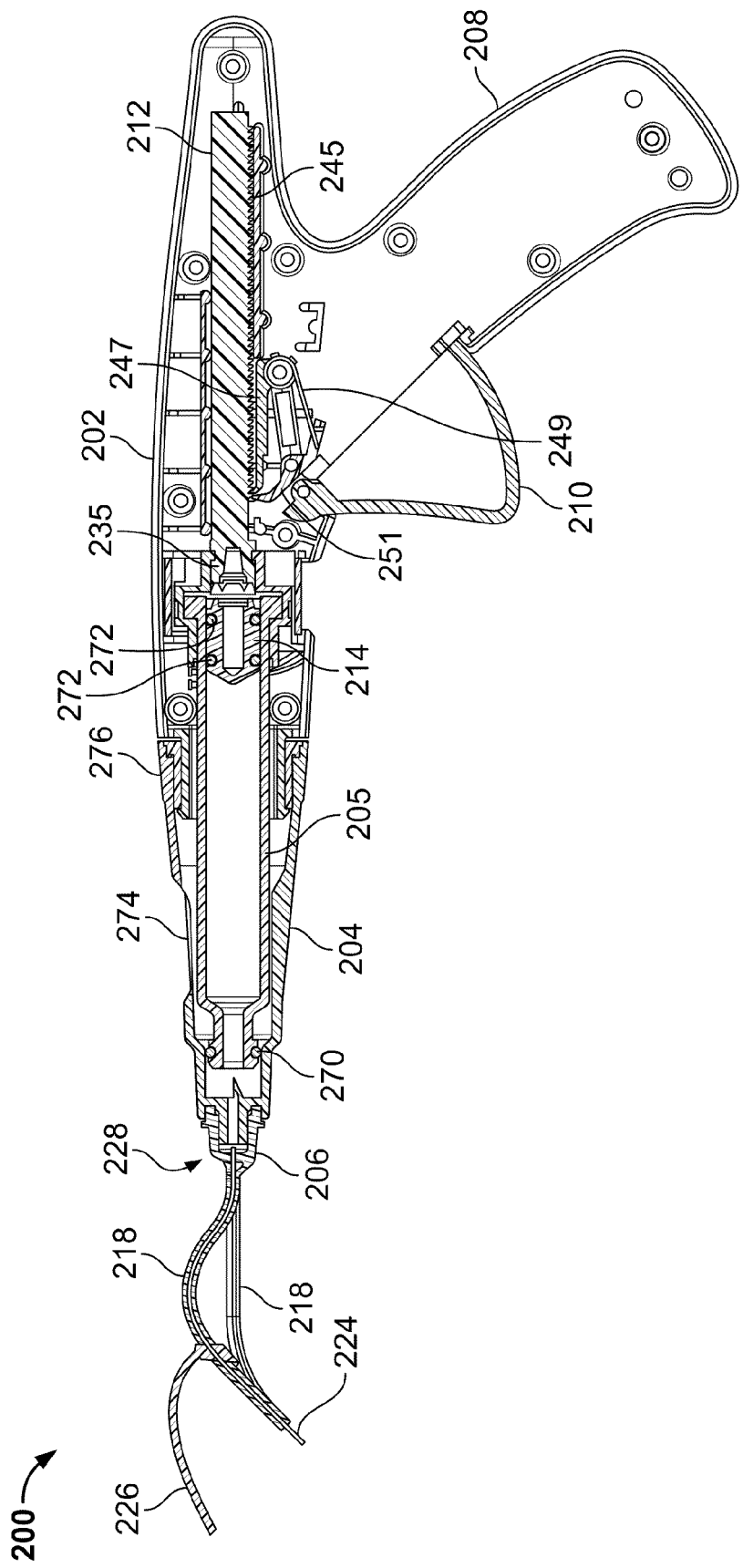
FIG. 8 is a cross-sectional view of an exemplary delivery device in accordance with some embodiments.

Referring to FIG. 7, delivery device 100 (as well as delivery device 200) can be configured such that multiple drops of viscous fluid are delivered to the targeted area of tissue per actuation. In some embodiments, one or more drops can be delivery simultaneously in a defined volume at predetermined spacing according to the number of supports 118 or 218. The user of delivery device 100 or 200 can apply a force to actuator 110 or 210 to advance the surgical adhesive and to delivery drops A, B, and C. After releasing actuator 110 or 210, the user can move delivery device 100 or 200 such that spacing gauge 126 or 226 is aligned with one of drops A, B, or C. Similarly, the user may align the right or left most support 118 or 218 with the left or right most drop to create additional column(s) of drops in a predetermined distance from the previous drops. In such circumstances, the user can apply a second force to actuator 110 or 210 to delivery a second row of drops a predetermined distance from drops A, B, and C. The user can continue to delivery drops of surgical adhesive in this manner until an appropriate or sufficient volume of adhesive has been applied to the targeted tissue area. In some embodiments, spacing gauge 126 or 226, which can project 2.0 cm distal to the row of supports 118 or 218, can provide a physical or visual reference for spacing drops of adhesive. For example, aligning spacing gauge 126 or 226 with the previously dispensed row of drops can position delivery tip 106 or 206 2.0 cm behind a previously delivered row of drops.

It should be understood from the description herein that, in some embodiments, the delivery devices provided herein (e.g., delivery devices 100 or 200) can be employed in other types of medical procedures in which a surgical adhesive is applied to a targeted area of tissue (e.g., during procedures such as facelifts, mastectomies, breast reduction, breast reconstruction, or the like).

In some embodiments, use of a delivery device provided herein can include a determination of whether a targeted tissue site is sufficiently covered with the drops of the surgical adhesive. If yes, the user can discard delivery device 100 or 200 after the single usage. In such circumstances, delivery device 100 or 200 can be discarded without reuse of delivery device 100 or 200 or any remaining portion of the surgical adhesive left in the adhesive cartridge.

If the targeted tissue site is not sufficiently covered with the surgical adhesive but delivery device 100 or 200 is exhausted, delivery device 100 or 200 can be discarded after the single usage. A second (new) delivery device 100 or 200 can be prepared for dispensation of more surgical adhesive to the targeted tissue site. Delivery tip 106 (or 206) of second delivery device 100 (or 200) can be directed toward the targeted tissue site. Thereafter, actuation of the device and delivery of the adhesive can proceed so that the drops of surgical adhesive are dispensed from second delivery device 100 (or 200) onto the targeted tissue site. For use in such circumstances, delivery device 100 (or 200) can be configured to be a disposable and non-reusable device. Following use of the delivery device, it can be discarded in a prompt and sanitary manner.

A process for manufacturing one or more of delivery devices provided herein (e.g., delivery devices 100 or 200) may include preparing cartridge housing 104 or 204 and assembling delivery tip 106 or 206 and internal components. The process of manufacturing delivery device 100 or 200 may also include the operation of sealing assembled delivery device 100 or 200 into a disposable storage pouch or tray. The disposable storage pouch or tray can be used to reduce the likelihood of contamination during storage or transport. In some circumstances, the storage pouch or tray can also contain instructions for use of the delivery devices. Alternatively, the storage pouch or tray can include instructions printed onto a surface of the storage pouch or tray.

The delivery devices provided herein (e.g., delivery device 100 or 200) can undergo a sterilization process so that the surgical adhesive therein is sterilized. In one example, the surgical adhesive can be sterilized using a gamma radiation device after a delivery device provided herein (e.g., delivery device 100 or 200) is sealed in the storage pouch or tray. Furthermore, the process can include the operation of packaging an assembled delivery device provided herein (e.g., assembled delivery device 100 or 200) in a storage container along with other delivery devices. For example, one or more delivery devices provided herein can be part of a packaged system that permits delivery devices to be readily available to the surgeon or other practitioner in a safe and reliable manner. Sets of delivery devices may be arranged in a surgical storage module, which can be readily received from a supplier and then fit into a surgical instrument rack for immediate or subsequent use in a surgical environment. Such a configuration can reduce the burden of staff workers responsible for material handling and inventory restocking. As previously described, some embodiments of the delivery devices provided herein may have a storage life of about 6 months to about 24 months, and about 12 months in this embodiment. In some circumstances, delivery devices, the storage container, or both may be labeled with an expiration date so as to notify the practitioner of the estimated useful life of each delivery device.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A delivery device for applying two or more drops of a high viscosity surgical adhesive to an anatomical tissue surface, wherein said delivery device comprises:
   (a) an actuator portion comprising an actuator and a push rod, wherein said actuator portion is configured to advance said push rod when a user actuates said actuator,
   (b) a cartridge housing configured to receive a cartridge containing said high viscosity surgical adhesive, wherein said cartridge housing is attached to said actuator portion such that said push rod is capable of advancing into said cartridge when said cartridge is positioned within said cartridge housing, and
   (c) a tip releasably engaged to said cartridge housing, wherein said tip comprises two or more channels and two or more tubular members, wherein at least a portion of each of said two or more tubular members is disposed within said channels, wherein at least a portion of at least one of the two or more channels has a non-linear shape, and wherein said tubular members are configured to allow said high viscosity surgical adhesive to move from said cartridge to said anatomical tissue surface when said user actuates said actuator, wherein a single actuation of said actuator is capable of dispensing a single drop of said high viscosity surgical adhesive from a distal tip of each of said tubular members at the same time, wherein the volume of each of said dispensed drops is substantially similar.

2. The delivery device of claim 1, wherein said high viscosity surgical adhesive has a viscosity that is from 200 cP to 2,000 cP.

3. The delivery device of claim 1, wherein said tip comprises three channels and three tubular members, wherein each tubular member is at least partially disposed within one and only one channel, and wherein each channel has disposed therein at least a portion of one and only one tubular member.

4. The delivery device of claim 3, wherein at least a first tubular member of the three tubular members has a serpentine shape.

5. The delivery device of claim 4, wherein said distal tips of said tubular members are configured in a linear line and are sequentially spaced apart from each other at a substantially similar distance, and wherein said tubular members have substantially similar lengths.

6. The delivery device of claim 5, wherein said tip comprises a spacing gauge configured to allow said user to align a second set of dispensed drops a predefined distance from a first set of dispensed drops.

7. The delivery device of claim 6, wherein a distal tip of said spacing gauge is positioned, from said linear line, at a distance similar to said substantially similar distance.

8. The delivery device of claim 1, wherein said tip comprises a spacing gauge configured to allow said user to align a second set of dispensed drops a predefined distance from a first set of dispensed drops.

9. The delivery device of claim 1, wherein said cartridge comprises a distal end, a proximal end, and a plunger located within said cartridge near to said proximal end, wherein said proximal end comprises a seal, and wherein said push rod is configured to engage said plunger.

10. The delivery device of claim 9, wherein a distal end of said push rod comprises a seal piercing element.

11. A delivery device for applying two or more drops of a high viscosity surgical adhesive to an anatomical tissue surface, wherein said delivery device comprises:
(a) a push rod,
(b) an actuator, wherein said actuator is configured to advance said push rod when a user actuates said actuator,
(c) a cartridge housing portion configured to house a cartridge containing said high viscosity surgical adhesive, wherein said push rod is capable of advancing into said cartridge when said cartridge is positioned within said cartridge housing, and
(d) a tip located at a distal end of said delivery device, wherein said tip comprises two or more channels and two or more tubular members, wherein at least about 25% of a length of each of said two or more tubular members is disposed within said channels, wherein at least a portion of at least one of the two or more channels is an open channel, and wherein said tubular members are configured to allow said high viscosity surgical adhesive to move from said cartridge to said anatomical tissue surface when said user actuates said actuator,
wherein a single actuation of said actuator is capable of dispensing a single drop of said high viscosity surgical adhesive from each of said tubular members at the same time, wherein the volume of each of said dispensed drops is substantially similar.

12. The delivery device of claim 11, wherein said high viscosity surgical adhesive has a viscosity that is from 200 cP to 2,000 cP.

13. The delivery device of claim 11, wherein said cartridge comprises a distal end, a proximal end, and a plunger located within said cartridge near to said proximal end, wherein said proximal end comprises a seal, and wherein said push rod is configured to engage said plunger.

14. The delivery device of claim 13, wherein a distal end of said push rod comprises a seal piercing element.

15. The delivery device of claim 14, wherein said seal piercing element comprises at least six extensions.

16. The delivery device of claim 14, wherein said seal piercing element is configured to pierce said seal of said proximal end of said cartridge.

17. The delivery device of claim 11, wherein said cartridge comprises a distal end and a proximal end, wherein said distal end comprises a seal, and wherein a distal portion of said delivery device comprises a piercing element configured to pierce said seal of said distal end of said cartridge as said cartridge is advanced from one location within said cartridge housing toward the distal end of said cartridge housing.

18. The delivery device of claim 17, wherein said delivery device comprises an actuator ring configured to advance said cartridge from one location within said cartridge housing toward the distal end of said cartridge housing as said actuator ring is rotated.

\* \* \* \* \*

UNITED STATES PATENT AND TRADEMARK OFFICE
CERTIFICATE OF CORRECTION

| | | |
|---|---|---|
| PATENT NO. | : 8,950,629 B2 | Page 1 of 1 |
| APPLICATION NO. | : 12/783378 | |
| DATED | : February 10, 2015 | |
| INVENTOR(S) | : Jeffrey S. Kapec et al. | |

It is certified that error appears in the above-identified patent and that said Letters Patent is hereby corrected as shown below:

On the Title Page

Item (75), please delete inventor "Gerhard Liepold".

Signed and Sealed this
Ninth Day of June, 2015

Michelle K. Lee
*Director of the United States Patent and Trademark Office*